(12) United States Patent
Masunaga et al.

(10) Patent No.: US 8,470,512 B2
(45) Date of Patent: Jun. 25, 2013

(54) POLYMER, CHEMICALLY AMPLIFIED NEGATIVE RESIST COMPOSITION, AND PATTERNING PROCESS

(75) Inventors: Keiichi Masunaga, Joetsu (JP); Satoshi Watanabe, Joetsu (JP); Akinobu Tanaka, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 26 days.

(21) Appl. No.: 13/192,297

(22) Filed: Jul. 27, 2011

(65) Prior Publication Data

US 2012/0028190 A1 Feb. 2, 2012

(30) Foreign Application Priority Data

Jul. 28, 2010 (JP) ................................. 2010-169482

(51) Int. Cl.
*G03F 7/038* (2006.01)
*G03F 7/32* (2006.01)
*C08F 26/06* (2006.01)

(52) U.S. Cl.
USPC ............. 430/270.1; 430/5; 430/325; 526/258

(58) Field of Classification Search
None
See application file for complete search history.

(56) References Cited

U.S. PATENT DOCUMENTS

| 5,618,892 | A | 4/1997 | Furihata et al. |
| 6,074,801 | A | 6/2000 | Iwasa et al. |
| 6,437,052 | B1 | 8/2002 | Iwasa et al. |
| 7,569,326 | B2 | 8/2009 | Ohsawa et al. |
| 7,977,027 | B2 | 7/2011 | Takeda et al. |
| 2006/0166133 | A1 | 7/2006 | Koitabashi et al. |
| 2008/0241751 | A1 | 10/2008 | Takeda et al. |
| 2009/0142698 | A1 | 6/2009 | Iwashita et al. |
| 2011/0143266 | A1* | 6/2011 | Tanaka et al. ..................... 430/5 |
| 2012/0029193 | A1* | 2/2012 | Domon et al. ................. 544/314 |
| 2012/0219887 | A1* | 8/2012 | Masunaga et al. ................ 430/5 |
| 2012/0219888 | A1* | 8/2012 | Masunaga et al. ................ 430/5 |

FOREIGN PATENT DOCUMENTS

| JP | 8-202037 A | 8/1996 |
| JP | 2001-226430 A | 8/2001 |
| JP | 2006-201532 A | 8/2006 |
| JP | 2006-215180 A | 8/2006 |
| JP | 2008-102383 A | 5/2008 |
| JP | 2008-133448 A | 6/2008 |
| JP | 2008-249762 A | 7/2011 |

OTHER PUBLICATIONS

English translation of JP, 2001-226430, A (2001) from machine translation from AIPN Japan Patent Office National Center for Industrial Property Information and Training, generated Sep. 25, 2012, 10 pages.*
English translation of JP, 2006-215180, A (2006) from machine translation from AIPN Japan Patent Office National Center for Industrial Property Information and Training, generated Sep. 25, 2012, 63 pages.*
European Search Report dated Oct. 10, 2011, issued in corresponding European Patent Application No. 11175294.5.
R. Ballini et al., "TBD-catalysed solventless syntehsis of symmetrically N,N'-substituted ureas from primary amines and diethyl carbonate", Royal Society of Chemistry, Green Chemistry, 2003, vol. 5, pp. 396-398, cited in spec.

* cited by examiner

*Primary Examiner* — Cynthia Hamilton
(74) *Attorney, Agent, or Firm* — Westerman, Hattori, Daniels & Adrian, LLP

(57) ABSTRACT

A polymer is provided comprising recurring units having a N,N'-bis(alkoxymethyl)tetrahydropyrimidinone or N,N'-bis(hydroxymethyl)tetrahydropyrimidinone structure on a side chain. When a chemically amplified negative resist composition is formulated using the polymer and processed by lithography, a fine resist pattern can be formed with the advantages of improved LER and high resolution.

10 Claims, No Drawings

POLYMER, CHEMICALLY AMPLIFIED NEGATIVE RESIST COMPOSITION, AND PATTERNING PROCESS

CROSS-REFERENCE TO RELATED APPLICATION

This non-provisional application claims priority under 35 U.S.C. §119(a) on Patent Application No. 2010-169482 filed in Japan on Jul. 28, 2010, the entire contents of which are hereby incorporated by reference.

TECHNICAL FIELD

This invention relates to a polymer, a chemically amplified negative resist composition comprising the polymer, and a pattern forming process using the composition.

BACKGROUND ART

To meet the recent demand for higher integration in integrated circuits, a finer feature size is required for pattern formation. In forming resist patterns with a feature size of 0.2 µm or less, chemically amplified resist compositions utilizing photo-generated acid as the catalyst are typically used in the art because of high sensitivity and resolution. Often, high-energy radiation such as UV, deep UV, EUV or electron beam (EB) is used as the light source for exposure of these resist compositions. Among others, the EB or EUV lithography is recognized most attractive because ultra-fine patterns are expectable.

Resist compositions include positive ones in which exposed areas are dissolved away and negative ones in which exposed areas are left as a pattern. A suitable composition is selected among them depending on the desired resist pattern. In general, the chemically amplified negative resist composition comprises a polymer which is normally soluble in an aqueous alkaline developer, an acid generator which is decomposed to generate an acid upon exposure to light, and a crosslinker which causes the polymer to crosslink between molecules in the presence of the acid serving as a catalyst, thus rendering the polymer insoluble in the developer. Typically a basic compound is added for controlling the diffusion of the acid generated upon light exposure.

A number of negative resist compositions of the type comprising a polymer which is soluble in an aqueous alkaline developer and includes phenolic units as the alkali-soluble units were developed, especially for the KrF excimer laser lithography. These compositions have not been used in the ArF excimer laser lithography because the phenolic units are not transmissive to exposure light having a wavelength of 150 to 220 nm. Recently, these compositions are recognized attractive again as the negative resist composition for the EB and EUV lithography capable of forming ultra-fine patterns. Exemplary compositions are described in JP-A 2006-201532, JP-A 2006-215180, and JP-A 2008-249762.

CITATION LIST

Patent Document 1: JP-A 2006-201532 (US 20060166133, EP 1684118, CN 1825206)
Patent Document 2: JP-A 2006-215180
Patent Document 3: JP-A 2008-249762
Patent Document 4: JP-A H08-202037
Patent Document 5: JP-A 2001-226430
Patent Document 6: JP-A 2008-133448
Patent Document 7: JP-A 2008-102383

DISCLOSURE OF THE INVENTION

To meet the requirement to reduce the feature size of the pattern, many improvements are made in negative resist compositions of the type using hydroxystyrene units typical of phenolic units. As the pattern size becomes as fine as 0.1 µm or less, it becomes more important than ever to reduce the line edge roughness (LER) of a fine pattern. The LER may be improved to some extent by reducing the sensitivity of resist film. However, for the EB lithography which is expected to form an ultra-fine pattern, but takes a long time for image writing as compared with the KrF and ArF lithography, the resist film is rather required to have a high sensitivity in order to improve throughputs.

It may also contribute to a reduction of LER to reduce the molecular weight of a base polymer. However, since a negative resist composition is designed such that the exposed region is insolubilized by crosslinking the base polymer to increase its molecular weight, the reduced molecular weight of the base polymer indicates a need for further acceleration of crosslinking reaction. As a result, the resist film is reduced in sensitivity. The throughput of image writing is accordingly reduced.

Many attempts were made to overcome the above-discussed problems of LER and throughput. In an attempt to form a pattern having a line width of 0.1 µm or less using a thin resist film having a thickness of 100 nm or less, few desirable properties are available from a combination of prior art materials. There is a demand for certain improvements.

An object of the invention is to provide a polymer which when used as one component in a chemically amplified negative resist composition, can be processed to form a pattern with a reduced LER, and display a practically acceptable sensitivity despite a low molecular weight during the process. Another object is to provide a chemically amplified negative resist composition comprising the polymer, and a pattern forming process using the composition.

The inventors have found that a polymer comprising recurring units having a N,N'-bis(alkoxymethyl)tetrahydro-pyrimidinone or N,N'-bis(hydroxymethyl)tetrahydropyrimidinone structure on a side chain, represented by the general formula (1) and/or (2), shown below, can be prepared; and that a chemically amplified negative resist composition comprising the polymer has the advantages of reduced LER and high resolution when it is processed to form a pattern.

In one aspect, the invention provides a polymer comprising recurring units of at least one type selected from recurring units having a N,N'-bis(alkoxymethyl)tetrahydropyrimidinone or N,N'-bis(hydroxymethyl)tetrahydropyrimidinone structure on a side chain, represented by the general formulae (1) and (2).

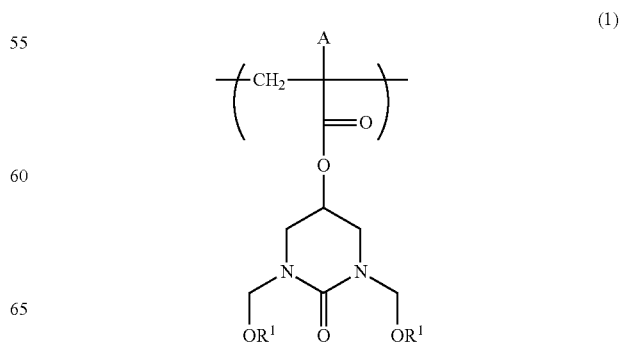

-continued

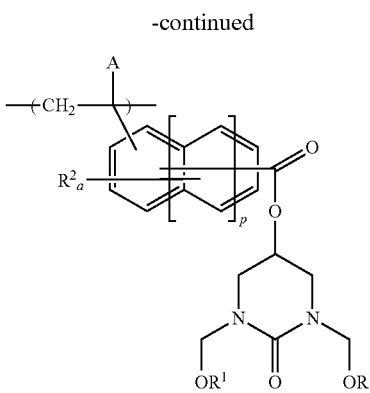

(2)

Herein A is hydrogen, fluorine, methyl or trifluoromethyl, $R^1$ is hydrogen or a monovalent, straight, branched or cyclic $C_1$-$C_6$ hydrocarbon group, $R^2$ is each independently a monovalent, straight, branched or cyclic $C_1$-$C_6$ hydrocarbon group which may contain oxygen, or halogen, a is an integer of 0 to 4, and p is an integer of 0 to 2.

In a preferred embodiment, the polymer may further comprise recurring units having the general formula (3).

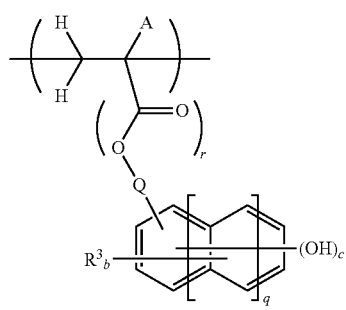

(3)

Herein A is as defined above, Q is a single bond, methylene group, or $C_2$-$C_{10}$ alkylene group which may contain an ether bond at an intermediate of the chain, $R^3$ is each independently a straight, branched or cyclic $C_1$-$C_6$ alkyl group, b is an integer of 0 to 4, c is an integer of 1 to 5, r is 0 or 1, and q is an integer of 0 to 2.

In another preferred embodiment, the polymer may further comprise recurring units of at least one type selected from recurring units represented by the general formulae (4) and (5).

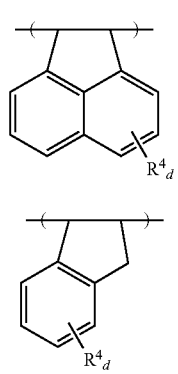

(4)

(5)

Herein $R^4$ is each independently hydroxyl, halogen, an optionally halo-substituted, straight, branched or cyclic $C_2$-$C_8$ acyloxy group, an optionally halo-substituted, straight, branched or cyclic $C_1$-$C_6$ alkyl group, or an optionally halo-substituted, straight, branched or cyclic $C_1$-$C_6$ alkoxy group, and d is an integer of 0 to 4.

In a further preferred embodiment, the polymer may further comprise recurring units having the general formula (6).

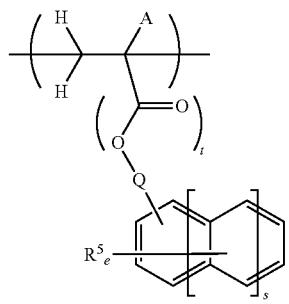

(6)

Herein A and Q are as defined above, $R^5$ is halogen, an optionally halo-substituted monovalent $C_1$-$C_{20}$ hydrocarbon or hydrocarbonoxy group, or a monovalent $C_2$-$C_{15}$ hydrocarbon-carbonyloxy group, t is 0 or 1, s is an integer of 0 to 2, and e is an integer of 0 to 5.

In another aspect, the invention provides a chemically amplified negative resist composition comprising the polymer defined above as a base polymer.

The resist composition may further comprise a polymer free of recurring units represented by formulae (1) and (2) as a base polymer. The polymer free of recurring units represented by formulae (1) and (2) is preferably a polymer comprising recurring units of at least one type selected from recurring units represented by formulae (3) to (6).

Also, a chemically amplified negative resist composition may comprise the polymer defined above as a crosslinker.

In a further aspect, the invention provides a process for forming a pattern, comprising the steps of applying the chemically amplified negative resist composition defined above onto a processable substrate to form a resist film, exposing patternwise the resist film to high-energy radiation, and developing the exposed resist film with an alkaline developer. Typically the processable substrate is a photomask blank.

ADVANTAGEOUS EFFECTS OF INVENTION

According to the invention, there is available a polymer comprising recurring units having a N,N'-bis(alkoxymethyl)tetrahydropyrimidinone or N,N'-bis(hydroxymethyl)tetrahydropyrimidinone structure on a side chain, represented by formula (1) and/or (2). When a chemically amplified negative resist composition is formulated using the polymer and processed by lithography, a negative fine resist pattern with an improved LER can be formed at a high resolution.

DESCRIPTION OF EMBODIMENTS

The terms "a" and "an" herein do not denote a limitation of quantity, but rather denote the presence of at least one of the referenced item. "Optional" or "optionally" means that the subsequently described event or circumstances may or may not occur, and that description includes instances where the event or circumstance occurs and instances where it does not. As used herein, the notation ($C_n$—$C_m$) means a group containing from n to m carbon atoms per group. The acronym "LER" stands for line edge roughness, "PAG" for photoacid generator, and "PEB" for post-exposure bake.

Polymer

One embodiment of the invention is a polymer or high molecular weight compound comprising recurring units of at least one type selected from recurring units having a N,N'-bis (alkoxymethyl)tetrahydropyrimidinone or N,N'-bis(hydroxymethyl)tetrahydropyrimidinone structure on a side chain, represented by the general formulae (1) and (2).

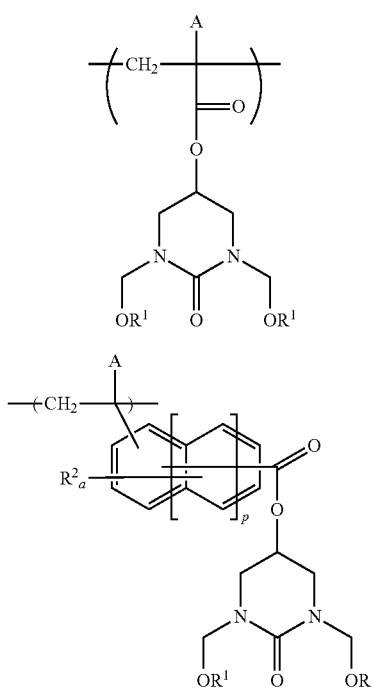

Herein, A is hydrogen, fluorine, methyl or trifluoromethyl, $R^1$ is hydrogen or a monovalent, straight, branched or cyclic $C_1$-$C_6$ hydrocarbon group, $R^2$ is each independently a monovalent, straight, branched or cyclic $C_1$-$C_6$ hydrocarbon group which may contain oxygen, or halogen, a is an integer of 0 to 4, and p is an integer of 0 to 2.

In formulae (1) and (2), A is hydrogen, fluorine, methyl or trifluoromethyl.

In formulae (1) and (2), $R^1$ is hydrogen or a monovalent, straight, branched or cyclic $C_1$-$C_6$ hydrocarbon group. Preferred examples of the monovalent, straight, branched or cyclic $C_1$-$C_6$ hydrocarbon group include alkyl groups such as methyl, ethyl, propyl, butyl, pentyl, hexyl and structural isomers thereof, cyclopentyl, and cyclohexyl. Inter alia, methyl is most preferred. A carbon count of more than 6 may lead to a lowering of crosslinking ability.

In formula (2), $R^2$ is each independently a monovalent, straight, branched or cyclic $C_1$-$C_6$ hydrocarbon group which may contain oxygen, or a halogen atom. Preferred examples of the monovalent, straight, branched or cyclic $C_1$-$C_6$ hydrocarbon group include alkyl groups such as methyl, ethyl, propyl, butyl, pentyl, hexyl and structural isomers thereof, cyclopentyl, and cyclohexyl. The monovalent hydrocarbon group may contain an oxygen atom, and examples of oxygen-containing hydrocarbon groups include alkoxy groups such as methoxy, ethoxy, propoxy, butoxy, pentyloxy, hexyloxy, and structural isomers of hydrocarbon moiety thereof, cyclopentyloxy, and cyclohexyloxy. Exemplary halogen atoms of $R^2$ are fluorine, chlorine, bromine and iodine.

Preferred, non-limiting examples of the recurring units having formulae (1) and (2) are shown below.

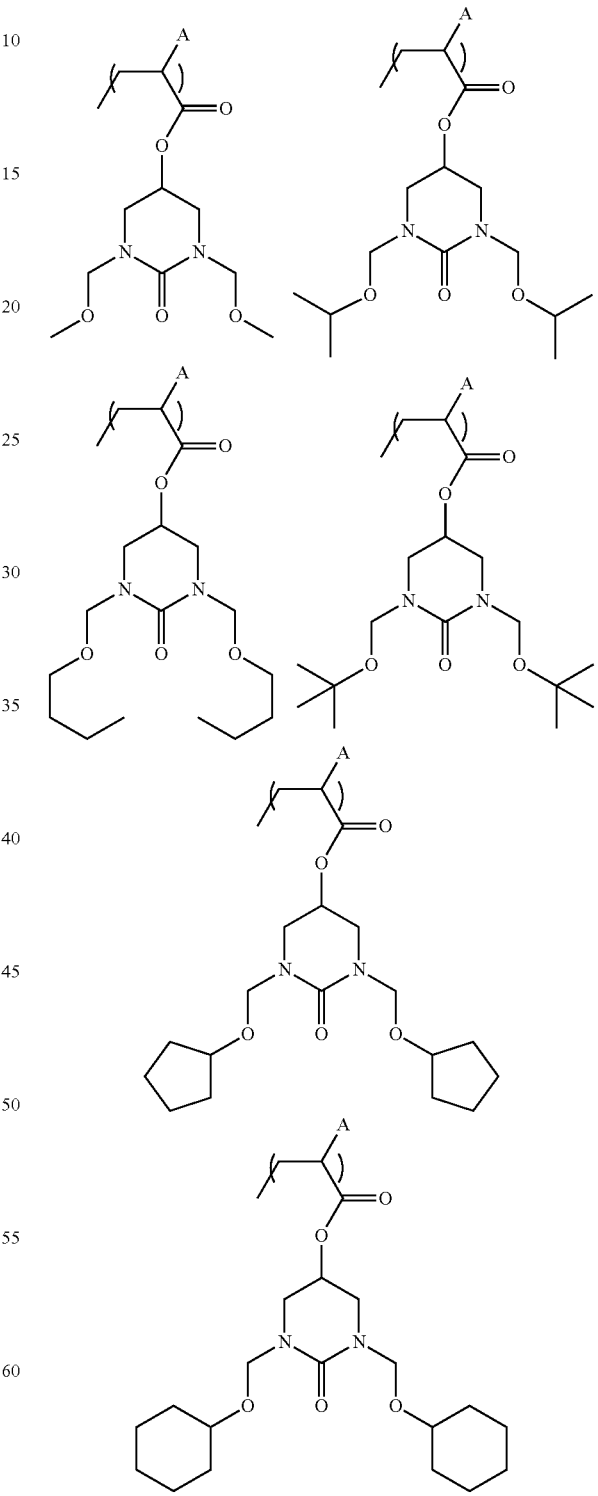

Herein A is as defined above.

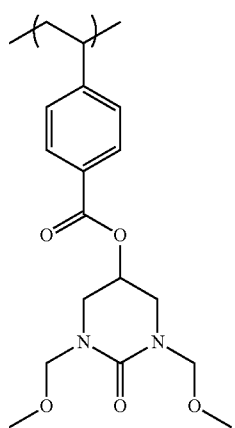
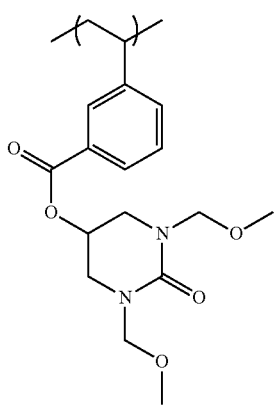
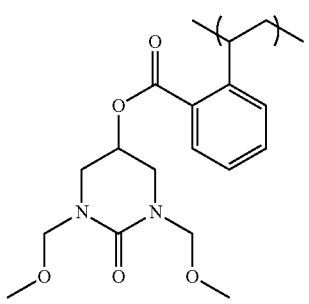
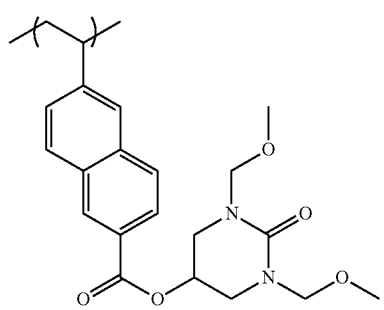
-continued
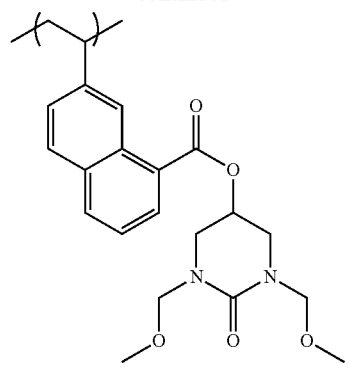
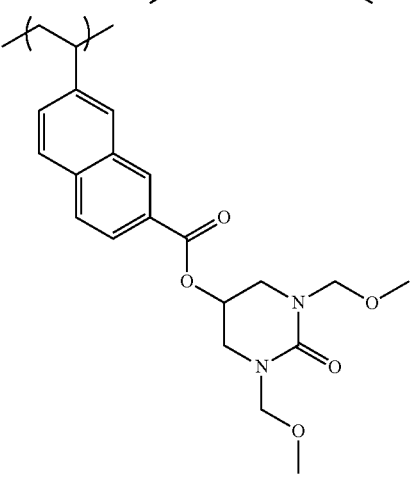
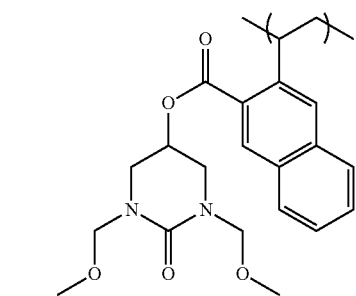
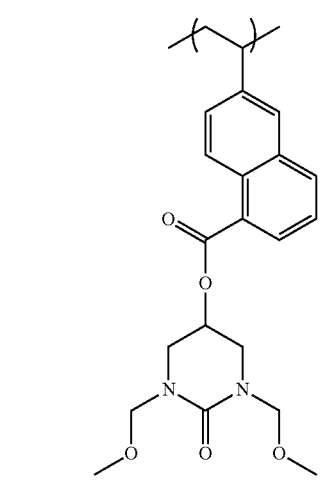

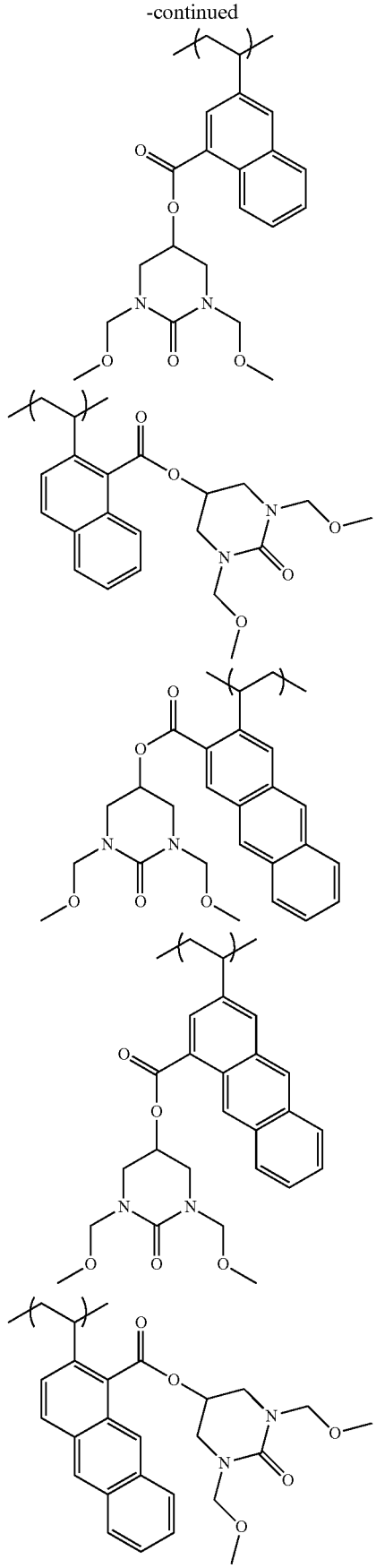
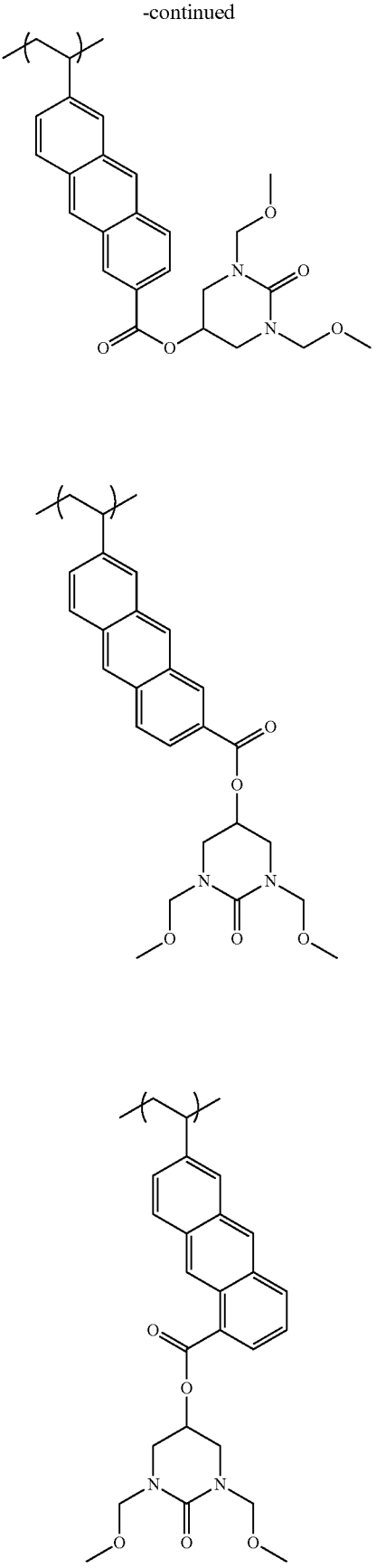

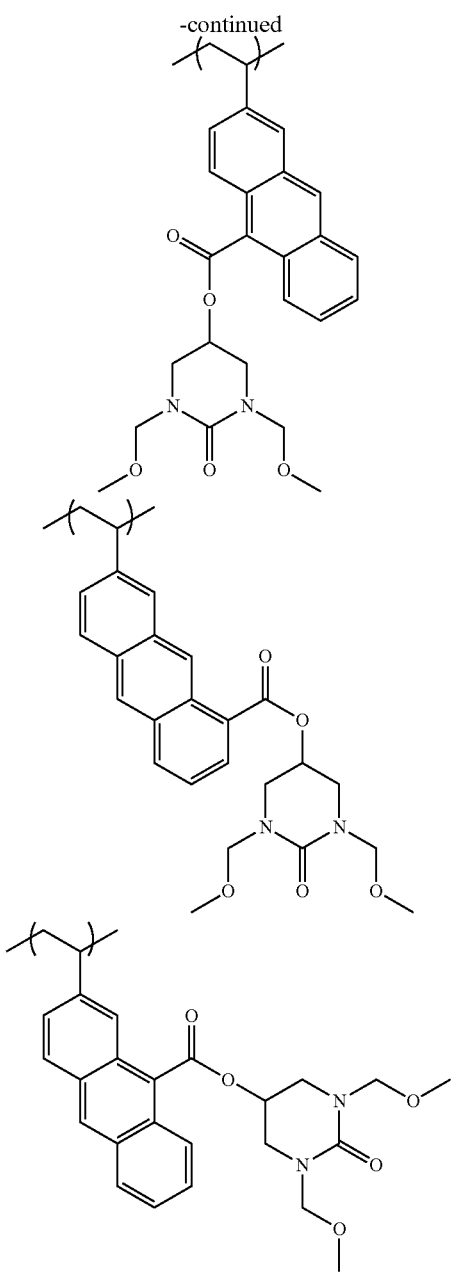

In formulae (1) and (2), the N,N'-bis(alkoxymethyl)tetrahydropyrimidinone structure has a function of becoming an active species for electrophilic reaction as a result of elimination of alcohol in the presence of an acid catalyst, to form a carbon-carbon bond or ether bond with a carbon atom of aromatic ring, an oxygen atom of hydroxyl group or the like. If the object with which the active species reacts is a polymer, the reaction leads to a higher molecular weight and even to a high degree of crosslinking which, if reached, leads to insolubilization in solvent. This is also true when the alkoxymethyl group substituting on the nitrogen atom in the N,N'-bis(alkoxymethyl)tetrahydropyrimidinone structure is replaced by a hydroxymethyl group. Notably, in the recurring units having a N,N'-bis(hydroxymethyl)tetrahydropyrimidinone structure on side chain, electrophilic reaction takes place along with elimination of water in the presence of an acid catalyst.

The above-mentioned reaction is a per se known negative toning mechanism that occurs between any of numerous acid-curable resins, especially polymers used in chemically amplified negative resist compositions, and a low molecular weight crosslinker in the presence of an acid catalyst. In contrast to the combination of a polymer with a low molecular weight crosslinker wherein electrophilic reaction occurs at more than one site to form crosslinks, the polymer of the invention forms a crosslink through a single reaction.

Prior art chemically amplified negative resist compositions using a polymer in combination with a low molecular weight crosslinker have a possibility that the crosslinker is not always dispersed uniformly upon film formation. The use of the inventive polymer minimizes the risk of the crosslinker being localized because the crosslinker is previously incorporated in the polymer. This is advantageous when it is desired to form a finer pattern structure uniformly.

Prior art attempts to introduce recurring units capable of forming crosslinks in the presence of an acid catalyst into polymers include introduction of a 2,4-diamino-5-triazine structure (Patent Document 4), and introduction of an oxirane structure (Patent Document 5). The N,N'-bis(alkoxymethyl)tetrahydropyrimidinone or N,N'-bis(hydroxymethyl)tetrahydropyrimidinone structure which is an active structure in the inventive polymer is an advantageous compound having such storage stability that it may undergo little or no changes of physical properties even when stored in solution form. The polymer is thus advantageously applicable to curable resin compositions relying on an acid catalyst mechanism as well as the chemically amplified negative resist composition to be described below.

The recurring units of formula (1) or (2) are derived from monomers having the following formula (1a).

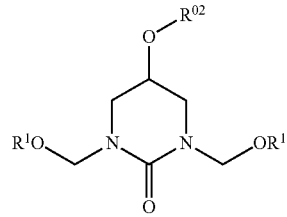

(1a)

Herein $R^1$ is hydrogen or a monovalent, straight, branched or cyclic $C_1$-$C_6$ hydrocarbon group, and $R^{02}$ is a group having the general formula (V-1) or (V-2).

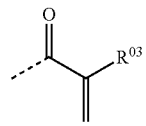

(V-1)

Herein $R^{03}$ is hydrogen, fluorine, methyl or trifluoromethyl, and the broken line denotes a valence bond to the oxygen atom.

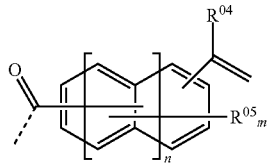

(V-2)

Herein $R^{04}$ is hydrogen or methyl, $R^{05}$ is each independently a monovalent, straight, branched or cyclic hydrocarbon group of 1 to 6 carbon atoms which may contain oxygen, or halogen, n is an integer of 0 to 2, m is an integer of 0 to (4+2n), and the broken line denotes a valence bond to the oxygen atom.

The monomer of formula (1a) from which crosslinkable recurring units having tetrahydropyrimidinone structure, represented by formula (1) or (2), are derived may be prepared, for example, according to the following scheme A, by forming a compound of formula (III) as an intermediate, and effecting reaction, typically esterification reaction, suitable to utilize a hydroxyl group of the intermediate, thereby forming a bond with a polymerizable unit suitable for use in predetermined polymerization reaction. Specifically as a typical polymerizable monomer from which recurring units of formula (1) are derived, an acrylic monomer wherein $R^1$ is monovalent hydrocarbon alkyl may be prepared according to the following scheme A although the method is not limited thereto.

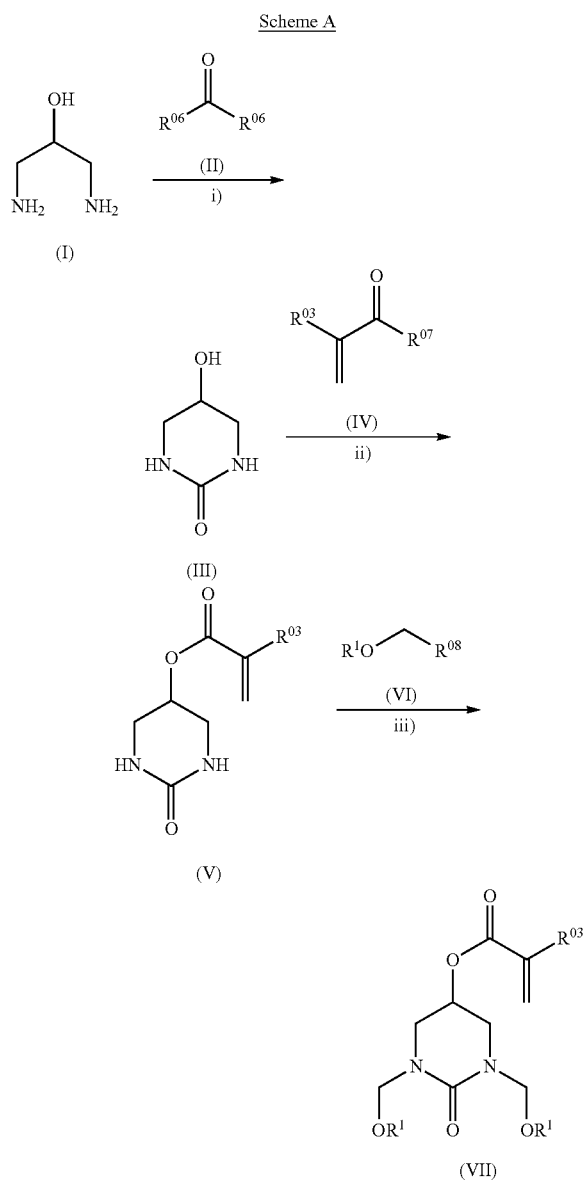

Herein $R^1$ and $R^{03}$ are as defined above, $R^{06}$ is methoxy or ethoxy, $R^{07}$ is halogen or a substituent group of the following formula:

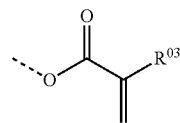

wherein $R^{03}$ is as defined above, and $R^{08}$ is halogen.

Scheme A is described in more detail. Step i) is to react 1,3-diamino-2-propanol with a carbonate (II) to form a cyclic urea (III). This reaction may be carried out by the well-known technique (Green Chemistry, Vol. 5, p 396-398, 2003, Royal Society of Chemistry). The reaction may be carried out in a solventless system or in water solvent, by adding 1,3-diamino-2-propanol, carbonate (II), and a base in sequence or at the same time, and optionally cooling or heating. Exemplary of the base are triethylamine, pyridine, 4-dimethylaminopyridine, 1,8-diazabicyclo[5.4.0]undec-7-ene or 1,5,7-triazabicyclo[4.4.0]dec-5-ene. At the end of reaction, the excess carbonate and the solvent were distilled off from the reaction mixture, yielding cyclic urea (III).

Step ii) is to bond a hydroxyl group of cyclic urea (III) with an acryloyl group, which may have a substituent group on double bond, to form an acryloyloxy cyclic urea (V). Reaction may be carried out by a standard technique, preferably by adding cyclic urea (III), acryloyl reagent (IV), and a base to a solvent in sequence or at the same time, and optionally cooling or heating. Typical of acryloyl reagent (IV) used herein are acid chlorides and acid anhydrides. An amount of acryloyl reagent (IV) used is preferably 0.5 to 10 moles, more preferably 1.0 to 5.0 moles per mole of cyclic urea (III).

Examples of the solvent which can be used for the reaction of step ii) include water, ethers such as tetrahydrofuran, diethyl ether, diisopropyl ether, di-n-butyl ether, and 1,4-dioxane, hydrocarbons such as n-hexane, n-heptane, benzene, toluene, and xylene, aprotic polar solvents such as acetonitrile, dimethyl sulfoxide (DMSO), and N,N-dimethylformamide (DMF), and chlorinated organic solvents such as methylene chloride, chloroform, and carbon tetrachloride. Any suitable solvent may be selected from these solvents depending on other reaction conditions while they may be used alone or in admixture. Examples of the base which can be used for the reaction of step ii) include amines such as ammonia, triethylamine, pyridine, lutidine, collidine, and N,N-dimethylaniline, hydroxides such as sodium hydroxide, potassium hydroxide and tetramethylammonium hydroxide, and carbonates such as potassium carbonate and sodium hydrogen carbonate. The bases may be used alone or in admixture.

The reaction temperature in step ii) is preferably from −70° C. to near the boiling point of the solvent used. An appropriate temperature may be selected depending on other reaction conditions, with a temperature of 0 to 30° C. being most preferred. Since noticeable side reactions like N-acryloyl formation may occur at higher temperatures, it is important for gaining higher yields that reaction be carried out at the permissible lowest temperature at which reaction takes place at a practically acceptable rate. The reaction time is preferably determined as appropriate for gaining higher yields by monitoring the progress of reaction by thin-layer chromatography (TLC) or gas chromatography (GC). Usually the reaction time is about 30 minutes to about 40 hours. The acryloyloxy cyclic urea (V) may be recovered from the reaction mixture by ordinary aqueous work-up. If necessary, the compound may be purified by standard techniques like distillation, recrystallization, and chromatography.

Step iii) is to alkoxymethylate the nitrogen atoms of acryloyloxy cyclic urea (V) to synthesize a crosslinker having a polymerizable functional group (VII). Reaction may be carried out by a standard technique, preferably by adding acryloyloxy cyclic urea (V), an alkoxymethyl halide (VI), and a base to a solvent in sequence or at the same time, and optionally cooling or heating. An amount of alkoxymethyl halide (VI) used is preferably 1.0 to 20 moles, more preferably 2.0 to 10.0 moles per mole of acryloyloxy cyclic urea (V).

Examples of the solvent which can be used for the reaction of step iii) include ethers such as tetrahydrofuran, diethyl ether, di-n-butyl ether, and 1,4-dioxane, hydrocarbons such as n-hexane, n-heptane, benzene, toluene, and xylene, aprotic polar solvents such as acetonitrile, dimethyl sulfoxide (DMSO), and N,N-dimethylformamide (DMF), and chlorinated organic solvents such as methylene chloride, chloroform, and carbon tetrachloride. Any suitable solvent may be selected from these solvents depending on other reaction conditions while they may be used alone or in admixture. Examples of the base which can be used for the reaction of step iii) include amines such as ammonia, triethylamine, diisopropylethylamine, pyridine, lutidine, collidine, and N,N-dimethylaniline, hydroxides such as sodium hydroxide, potassium hydroxide and tetramethylammonium hydroxide, and carbonates such as potassium carbonate and sodium hydrogen carbonate. The bases may be used alone or in admixture.

The reaction temperature in step iii) is preferably from −70° C. to near the boiling point of the solvent used. An appropriate temperature may be selected depending on other reaction conditions, with a temperature of 0 to 30° C. being most preferred. Since noticeable side reactions may occur at higher temperatures, it is important for gaining higher yields that reaction be carried out at the permissible lowest temperature at which reaction takes place at a practically acceptable rate. The reaction time is preferably determined as appropriate for gaining higher yields by monitoring the progress of reaction by TLC or GC. Usually the reaction time is about 30 minutes to about 40 hours. The crosslinkable monomer (VII) may be recovered from the reaction mixture by ordinary aqueous work-up. If necessary, the compound may be purified by standard techniques like distillation, recrystallization, and chromatography.

In order to produce a compound wherein $R^1$ is hydrogen as crosslinker (VII) according to the above scheme A, step iii) may be hydroxymethylation, which may be carried out by a well-known technique. Specifically, synthesis from acryloyloxy cyclic urea (V) may be carried out by adding acryloyloxy cyclic urea (V), paraformaldehyde or formalin instead of alkoxymethyl halide (VI), and an acid to a solvent in sequence or at the same time, and optionally cooling or heating. An amount of paraformaldehyde or formalin used is preferably 1.0 to 20 moles, more preferably 2.0 to 10.0 moles per mole of acryloyloxy cyclic urea (V).

Examples of the solvent which can be used for the hydroxymethylation reaction of step iii) include ethers such as tetrahydrofuran, diethyl ether, di-n-butyl ether, and 1,4-dioxane, hydrocarbons such as n-hexane, n-heptane, benzene, toluene, and xylene, aprotic polar solvents such as acetonitrile, dimethyl sulfoxide (DMSO), and N,N-dimethylformamide (DMF), and chlorinated organic solvents such as methylene chloride, chloroform, and carbon tetrachloride. Any suitable solvent may be selected from these solvents depending on other reaction conditions while they may be used alone or in admixture. Examples of the acid which can be used for the hydroxymethylation reaction of step iii) include mineral acids such as hydrochloric acid, sulfuric acid, nitric acid and perchloric acid, and organic acids such as p-toluenesulfonic acid, benzenesulfonic acid and trifluoroacetic acid. These acids may be used alone or in admixture.

The temperature of hydroxymethylation reaction in step iii) is preferably from −70° C. to near the boiling point of the solvent used. An appropriate temperature may be selected depending on other reaction conditions, with a temperature of 0 to 50° C. being most preferred. Since noticeable side reactions may occur at higher temperatures, it is important for gaining higher yields that reaction be carried out at the permissible lowest temperature at which reaction takes place at a practically acceptable rate. The reaction time is preferably determined as appropriate for gaining higher yields by monitoring the progress of reaction by TLC or GC. Usually the reaction time is about 30 minutes to about 40 hours. The crosslinker (VI) having a polymerizable functional group wherein $R^1$ is hydrogen may be recovered from the reaction mixture by ordinary aqueous work-up. If necessary, the compound may be purified by standard techniques like distillation, recrystallization, and chromatography.

A polymerizable monomer from which recurring units of formula (2) are derived may be prepared from the intermediate (III), for example, according to the following scheme B although the method is not limited thereto.

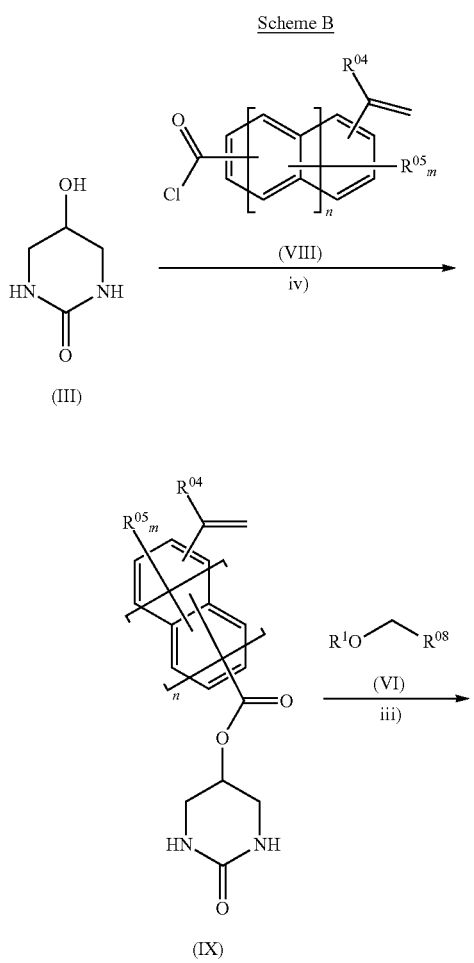

Scheme B

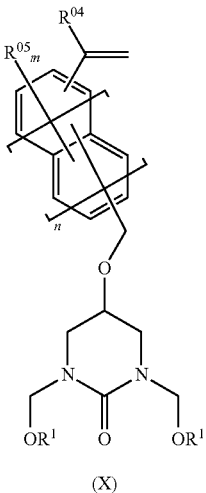

(X)

Herein $R^1$, $R^{04}$, $R^{05}$, $R^{08}$, n and m are as defined above.

In Scheme B, step iv) is to couple a hydroxyl group of cyclic urea (III) with a benzoyl group, whose aromatic ring may be substituted, to form a benzoyloxy cyclic urea (IX). Reaction may be carried out by a standard technique, preferably by adding cyclic urea (III), a benzoyl reagent (VIII), and a base to a solvent in sequence or at the same time, and optionally cooling or heating. Typical of benzoyl reagent (VIII) used herein are acid chlorides and acid anhydrides. An amount of benzoyl reagent (VIII) used is preferably 0.5 to 10 moles, more preferably 1.0 to 5.0 moles per mole of cyclic urea (III).

Examples of the solvent which can be used for the reaction of step iv) include water, ethers such as tetrahydrofuran, diethyl ether, diisopropyl ether, di-n-butyl ether, and 1,4-dioxane, hydrocarbons such as n-hexane, n-heptane, benzene, toluene, and xylene, aprotic polar solvents such as acetonitrile, dimethyl sulfoxide (DMSO), and N,N-dimethylformamide (DMF), and chlorinated organic solvents such as methylene chloride, chloroform, and carbon tetrachloride. Any suitable solvent may be selected from these solvents depending on other reaction conditions while they may be used alone or in admixture. Examples of the base which can be used for the reaction of step iv) include amines such as ammonia, triethylamine, pyridine, lutidine, collidine, and N,N-dimethylaniline, hydroxides such as sodium hydroxide, potassium hydroxide and tetramethylammonium hydroxide, and carbonates such as potassium carbonate and sodium hydrogen carbonate. The bases may be used alone or in admixture.

The reaction temperature in step iv) is preferably from −70° C. to near the boiling point of the solvent used. An appropriate temperature may be selected depending on other reaction conditions, with a temperature of 0 to 30° C. being most preferred. Since noticeable side reactions like N-benzoyl formation may occur at higher temperatures, it is important for gaining higher yields that reaction be carried out at the permissible lowest temperature at which reaction takes place at a practically acceptable rate. The reaction time is preferably determined as appropriate for gaining higher yields by monitoring the progress of reaction by TLC or GC. Usually the reaction time is about 30 minutes to about 40 hours. The benzoyloxy cyclic urea (IX) may be recovered from the reaction mixture by ordinary aqueous work-up. If necessary, it may be purified by standard techniques like distillation, recrystallization, and chromatography.

Subsequently, a crosslinkable monomer (X) wherein $R^{03}$ is a group of formula (V-2) may be produced by subjecting benzoyloxy cyclic urea (IX) to the reaction of step iii).

It is understood that monomers suited for various different polymer systems can be synthesized by applying the aforementioned method for monomer synthesis in different ways. For example, if the cyclic urea of formula (III) as the intermediate is combined with norbornenecarboxylic acid chloride, a monomer suited for use in the synthesis of norbornene based polymers is obtainable.

Most often, the polymer comprising recurring units of formula (1) and/or (2) is used as one component in a chemically amplified negative resist composition. In a preferred embodiment, recurring units of the following general formula (3) are further incorporated in the polymer as the recurring units for providing adhesion to substrate and dissolution in alkaline developer and capable of reaction with the recurring units of formula (1) and/or (2).

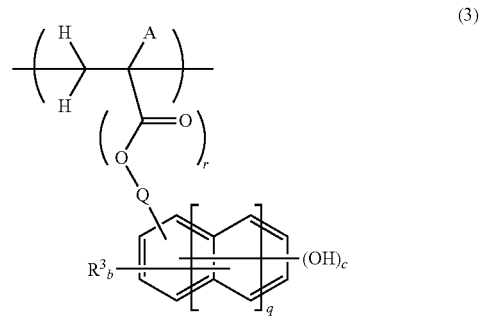

(3)

Herein A is as defined above, Q is a single bond, methylene group, or $C_2$-$C_{10}$ alkylene group which may contain an ether bond at an intermediate of the chain, $R^3$ is each independently a straight, branched or cyclic $C_1$-$C_6$ alkyl group, b is an integer of 0 to 4, c is an integer of 1 to 5, r is 0 or 1, and q is an integer of 0 to 2.

In formula (3), Q is a single bond, a methylene group, or a $C_2$-$C_{10}$ alkylene group which may contain an ether bond at an intermediate of the chain. Preferred examples of the alkylene group include ethylene, propylene, butylene, pentylene, hexylene, and structural isomers thereof having a carbon skeleton of branched or cyclic structure. When the alkylene group contains an ether bond, the ether bond may be located at any position excluding between α and β-carbons relative to the ester oxygen.

In formula (3), $R^3$ is each independently a straight, branched or cyclic $C_1$-$C_6$ alkyl group. Preferred examples of the $C_1$-$C_6$ alkyl groups include methyl, ethyl, propyl, isopropyl, butyl, pentyl, hexyl and structural isomers thereof having a carbon skeleton of branched or cyclic structure. A carbon count of more than 6 may lead to a lowering of solubility in alkaline developer.

In formula (3), r is 0 or 1, and q is an integer of 0 to 2. The structure represents a benzene skeleton when q=0, a naphthalene skeleton when q=1, and an anthracene skeleton when q=2. The subscript b is an integer of 0 to 4, and c is an integer of 1 to 5. In case of q=0, preferably b is an integer of 0 to 3 and c is an integer of 1 to 5. In case of q=1 or 2, preferably b is an integer of 0 to 4 and c is an integer of 1 to 5.

Of the recurring units of formula (3), those recurring units wherein r is 0 and Q is valent bond (meaning that the aromatic ring is directly bonded to the main chain of the polymer), that is, linker-free recurring units are units derived from monomers in which a 1-substituted or unsubstituted vinyl group is attached to a hydroxyl-substituted aromatic ring, as typified by hydroxystyrene units. Preferred examples include 3-hydroxystyrene, 4-hydroxystyrene, 5-hydroxy-2-vinylnaphthalene, and 6-hydroxy-2-vinylnaphthalene.

Those recurring units wherein r is 1, that is, recurring units having an ester structure as the linker are units of carbonyl-substituted vinyl monomers as typified by (meth)acrylates.

Preferred non-limiting examples of the units of formula (3) having a linker (—CO—O—Q-) derived from (meth)acrylates are shown below.

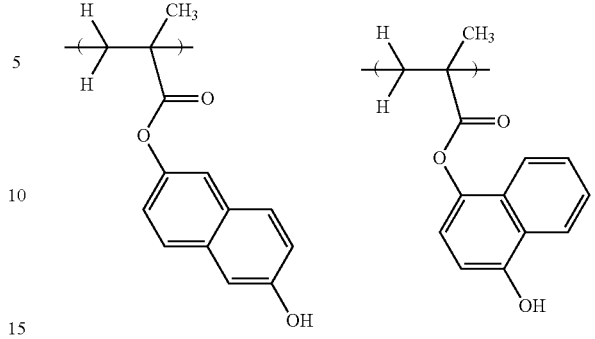

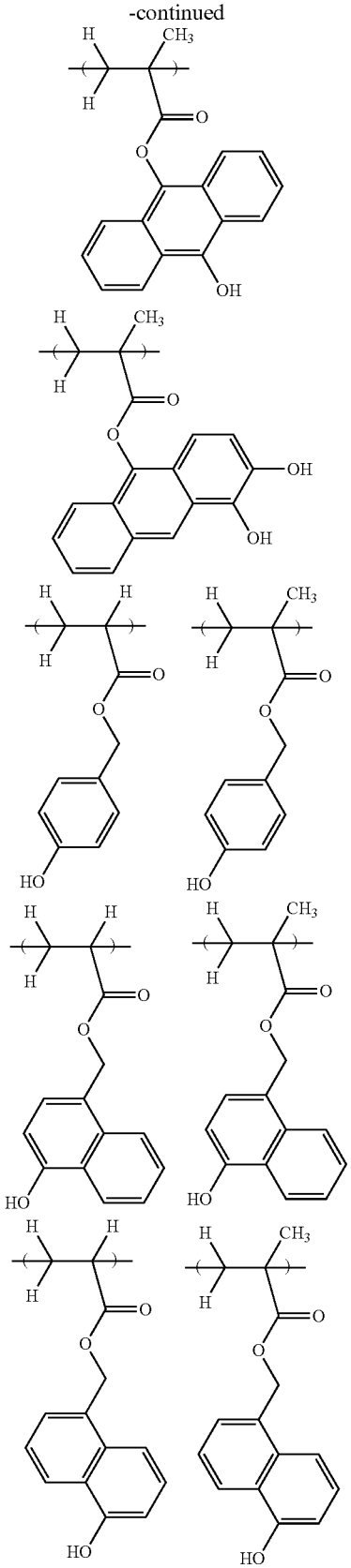

The polymer may further comprise recurring units having the general formula (4) and/or (5).

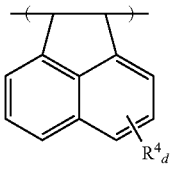

(4)

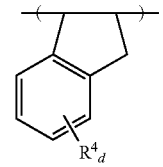

(5)

Herein $R^4$ is each independently hydroxyl, halogen, an optionally halo-substituted, straight, branched or cyclic $C_2$-$C_8$ acyloxy group, an optionally halo-substituted, straight, branched or cyclic $C_1$-$C_6$ alkyl group, or an optionally halo-substituted, straight, branched or cyclic $C_1$-$C_6$ alkoxy group, and d is an integer of 0 to 4. When the polymer comprising recurring units of formula (4) and/or (5) in addition to recurring units of formula (1) and/or (2) is used as one component in a chemically amplified negative resist composition, there are obtained the advantages that the aromatic ring included in the recurring unit of formula (4) or (5) provides etch resistance and the addition of cyclic structure to the main chain enhances resistance to EB irradiation during etching or pattern inspection.

In formulae (4) and (5), $R^4$ stands for halogen, examples of which include fluorine, chlorine and bromine. When $R^4$ stands for an optionally halo-substituted, straight, branched or cyclic $C_2$-$C_8$ acyloxy group, examples include acetoxy, ethylcarbonyloxy, propylcarbonyloxy, butylcarbonyloxy, pentylcarbonyloxy, hexylcarbonyloxy, isopropylcarbonyloxy, isobutylcarbonyloxy, tert-butylcarbonyloxy, cyclopentylcarbonyloxy, and cyclohexylcarbonyloxy. When $R^4$ stands for an optionally halo-substituted, straight, branched or cyclic $C_1$-$C_6$ alkyl group, examples include methyl, ethyl, propyl, butyl, pentyl, hexyl, isopropyl, and tert-butyl. When $R^4$ stands for an optionally halo-substituted, straight, branched or cyclic $C_1$-$C_6$ alkoxy group, examples include methoxy, ethoxy, propoxy, butoxy, isopropoxy, and tert-butoxy.

Preferred non-limiting examples of the compounds from which the recurring units of formulae (4) and (5) are derived are given below.

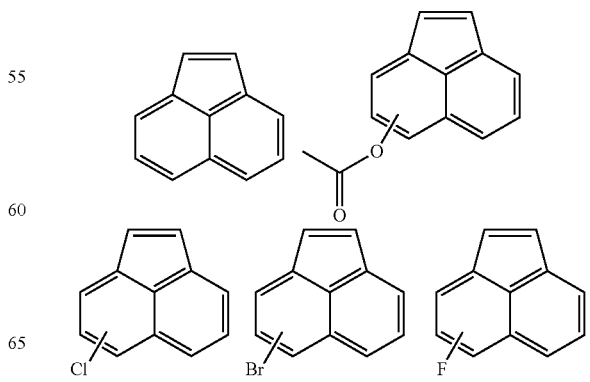

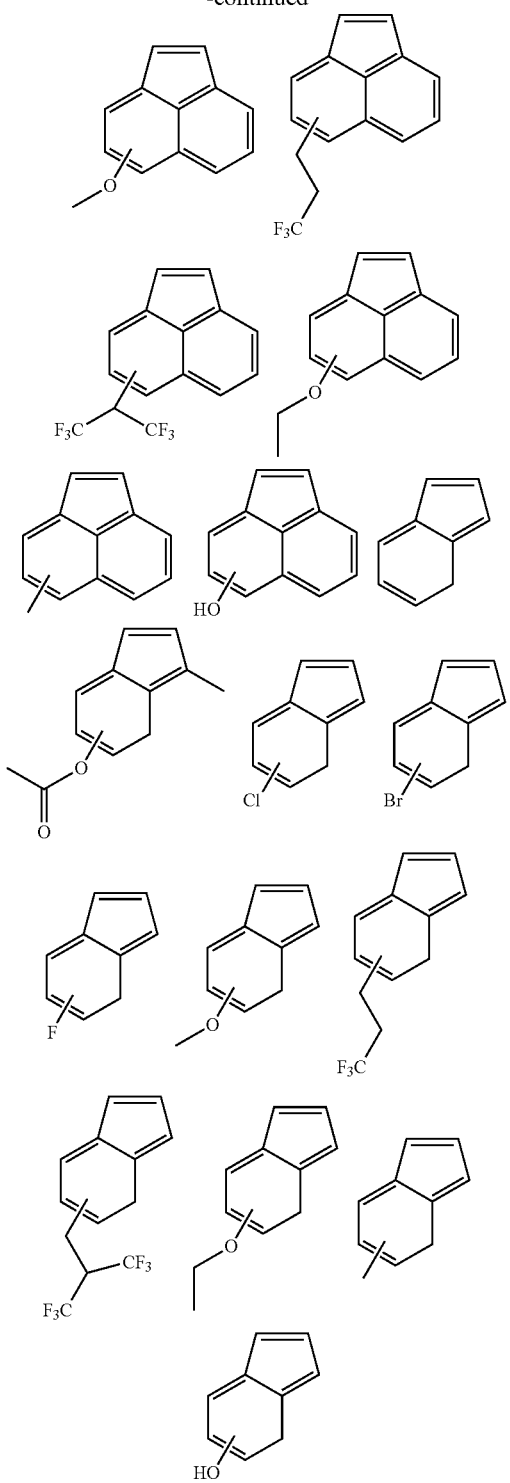

When the polymer comprising recurring units of formula (1) and/or (2) is used as one component in a chemically amplified negative resist composition, recurring units of the following general formula (6) may be incorporated in the polymer for the purpose of adjusting the solubility thereof in alkaline developer.

(6)

Herein A and Q are as defined above, $R^5$ is halogen, an optionally halo-substituted monovalent $C_1$-$C_{20}$ hydrocarbon or hydrocarbonoxy group, or a monovalent $C_2$-$C_{15}$ hydrocarbon-carbonyloxy group, t is 0 or 1, s is an integer of 0 to 2, and e is an integer of 0 to 5.

In formula (6), $R^5$ stands for halogen, examples of which include fluorine, chlorine and bromine. When $R^5$ stands for a monovalent hydrocarbon or hydrocarbonoxy group, the monovalent hydrocarbon group or the hydrocarbon moiety of the monovalent hydrocarbonoxy group may be an alkyl group, preferably of 1 to 20 carbon atoms, more preferably 1 to 10 carbon atoms, and even more preferably 1 to 8 carbon atoms, preferred examples of which include methyl, ethyl, propyl, butyl, pentyl, hexyl, heptyl, octyl and structural isomers thereof, cyclopentyl, cyclohexyl, and cyclooctyl. The monovalent hydrocarbon group or the hydrocarbon moiety of the monovalent hydrocarbonoxy group may also be an aromatic group, preferably an optionally substituted $C_6$-$C_{20}$ aromatic group, preferred examples of which include alkyl-substituted or unsubstituted phenyl, naphthyl, benzyloxy, naphthyloxy, and phenethyl. When $R^5$ stands for a monovalent $C_2$-$C_{15}$ hydrocarbon-carbonyloxy group, preferred examples include methylcarbonyloxy, ethylcarbonyloxy, propylcarbonyloxy, isopropylcarbonyloxy, cyclopentylcarbonyloxy, cyclohexylcarbonyloxy, cyclooctylcarbonyloxy, phenylcarbonyloxy, and naphthylcarbonyloxy.

In the embodiment wherein recurring units of formula (6) are incorporated as constituent units, there are obtained the advantages that the aromatic ring serves to provide etch resistance and adjust the dissolution rate of the polymer, and crosslinking reaction can be controlled by a choice of a suitable substituent group for $R^5$, for example, the degree of crosslink formation can be improved by selecting an alkoxy group for $R^5$, or the efficiency of crosslink formation can be adjusted by selecting alkyl and aromatic groups for $R^5$. This is a great contribution to the material design.

The polymer of the invention is advantageously used as a base polymer in a chemically amplified negative resist composition. The base polymer used in conventional chemically amplified negative resist compositions including the chemically amplified negative resist composition of the invention should be provided with a function of dissolution in an alkaline developer used in the development step, typically 2.38 wt % tetramethylammonium hydroxide aqueous solution, a function of adhesion to the substrate, and a function of reaction with a crosslinking functional group, and preferably further with a function of controlling solubility in alkaline developer and a function of providing higher etch resistance. The base polymer may be a single polymer in which recurring units having different functions are combined to provide for all the functions or a blend of two or more polymers which are combined so as to meet all the functions.

The base polymer may be a blend of different polymers as described just above. When such a blend is avoided, a polymer is designed by selecting recurring units having a particular function, and determining a ratio of respective recurring units so as to provide a better resolution when processed into a resist film.

In one embodiment wherein a single polymer comprising recurring units having formula (1) and/or (2) is used as the base polymer, the polymer design is made such that a content of the recurring units having formula (1) and/or (2) may fall preferably in the range of 1 to 40 mol %, more preferably 2 to 30 mol %, and even more preferably 5 to 15 mol % based on the entire recurring units of the polymer. If the content of recurring units having formula (1) and/or (2) is less than 1 mol %, benefits of significance may not be obtained. If the content is more than 40 mol %, the dissolution rate of unexposed region may become difficult to control or the efficiency of crosslink formation may be rather reduced.

The content of recurring units as additional constituent units must be adjusted depending on the structure of selected recurring units. For example, when recurring units of formula (3) are used as the recurring units for providing adhesion to the substrate and dissolution in alkaline developer, the polymer design is made such that the content of recurring units having formula (3) may be preferably at least 20 mol %, more preferably at least 30 mol % based on the entire recurring units of the polymer, with the upper limit being preferably 90 mol %, and more preferably 85 mol %, to provide an appropriate alkali solubility such that no residue may be left upon development, though the content varies with the strength of polarity, the fat solubility of aromatic ring, and the presence or absence of alkyl substituent group. If the content of recurring units having formula (3) is more than 90 mol %, an undercut phenomenon may occur upon fine pattern formation. The recurring units having formula (3) may be of one type or a mixture of plural types. Also, the recurring units having formula (3) may be replaced by the recurring units having formula (4) or (5) in which the substituent group is hydroxyl, as will be described later.

In another embodiment wherein the recurring units having formula (4) or (5) are used, the units may be of one type or a mixture of plural types. For the effect of improving etch resistance, the recurring units having formula (4) or (5) are preferably incorporated in a content of at least 5 mol %, more preferably at least 7 mol % based on the entire recurring units of the polymer. Where the functional group $R^4$ in formula (4) or (5) is hydroxyl, the upper limit of the content of the recurring units having formula (4) or (5) may be determined by merging it with the content of recurring units having formula (3) so that the total content may fall in the preferred range of recurring units having formula (3). Specifically, the upper limit of the content of the recurring units having formula (4) or (5) is up to 90 mol %, the upper limit of the preferred range of recurring units having formula (3). Where no functional group is included or the functional group is not hydroxyl, the content of the recurring units having formula (4) or (5) is preferably up to 30 mol %. If the content of the recurring units of formula (4) or (5) having no functional group or having a functional group other than hydroxyl is more than 30 mol %, it may cause development defects.

If pattern collapse or disruption arises from too high a dissolution rate of the base polymer in alkaline developer, it is recommended to add recurring units having formula (6) to improve resolution. Where the recurring units having formula (6) are incorporated in the polymer, the content of recurring units having formula (6) is preferably 3 to 40 mol %, more preferably 5 to 30 mol % based on the entire recurring units of the polymer. If this content is more than 40 mol %, residues may be left after development. Also, the recurring units having formula (6) may be of one type or a mixture of plural types.

When a polymer containing recurring units having formula (1) and/or (2) and further containing recurring units selected from formulae (3) to (6) as main constituent units is used as the base polymer, any of well-known recurring units may be incorporated as additional recurring units as long as the content is less than 50 mol %. Such additional recurring units include (meth)acrylate units having an oxirane ring serving as crosslinking units as described in JP-A 2001-226430, and (meth)acrylate units having an adhesive group such as lactone structure. These additional recurring units may be incorporated to enable fine adjustment of resist film properties although they need not be incorporated.

In another embodiment, the base polymer used in the chemically amplified negative resist composition is a blend of two or more polymers. It may be a blend of plural polymers comprising recurring units having formula (1) and/or (2), or a blend of a polymer comprising recurring units having formula (1) and/or (2) and a polymer free of such units. When polymers are used as a blend, the design of polymers is made on the basis that the polymer blend is dissolvable in an aqueous alkaline developer, such that the contents of recurring units having formulae (1) to (6) and other recurring units in the blend may fall in the respective ranges for the contents of recurring units having formulae (1) to (6) and other recurring units, defined above in conjunction with the polymer which is used alone as the base polymer.

The content of recurring units having formula (1) and/or (2) in the polymer blend as base polymer relative to the entire recurring units may fall in the preferred range defined above in conjunction with the polymer which is used alone as the base polymer. For this reason, the content of recurring units having formula (1) and/or (2) relative to the entire recurring units of a polymer prior to blending may vary over a wider range. For example, a homopolymer consisting of formula (1) or (2) units and having a weight average molecular weight (Mw) of up to 2,000 may be used as one member of a polymer blend, because polymer blending is adjustable such that the polymer blend may be dissolvable in an aqueous alkaline developer. It is noted that the weight average molecular weight (Mw) is determined by gel permeation chromatography (GPC) versus polystyrene standards.

When a polymer blend in which all polymers comprise recurring units having formula (1) and/or (2) is used as the base polymer, the another main contents of recurring units selected from formulae (3) to (6) in each polymer basically fall in the ranges defined above for the polymer which is used alone as the base polymer. A proper combination of preferred contents may be selected from the respective ranges.

When a blend of a polymer comprising recurring units having formula (1) and/or (2) and another polymer free of such units is used as the base polymer, the other polymer free of recurring units having formulae (1) and (2) may be any of well-known polymers which are used in conventional chemically amplified negative resist compositions and which are normally alkali soluble, but turn alkali insoluble upon exposure to high-energy radiation when combined with an acid generator and a crosslinker. However, the other polymer should not undergo phase separation when blended with the polymer comprising recurring units having formula (1). In this sense, a choice should be made among those polymers comprising recurring units of similar structure, but free of recurring units having formulae (1) and (2). For example, where a polymer containing recurring units having formula (1) and/or (2) and further containing recurring units selected from formulae (3) to (6) as main constituent units are properly combined is used as the polymer comprising recurring units having formula (1) and/or (2), the other polymer free of recurring units having formulae (1) and (2) preferably comprises constituent units selected from recurring units having formulae (3) to (6). A blend of a polymer in which most recurring units are derived from a (meth)acrylic monomer free of aromatic structure and a polymer in which most recurring units are derived from a styrenic monomer has a potential of phase separation, which may lead to a substantial roughness after development.

Where a polymer containing recurring units having formula (1) and/or (2) and further containing recurring units selected from formulae (3) to (6) as main constituent units are properly combined is used as the polymer comprising recurring units having formula (1) and/or (2), it is preferably blended with another polymer free of recurring units having formulae (1) and (2) in which recurring units selected from formulae (3) to (6) are combined, to form a polymer blend serving as the base polymer. Examples of the other polymer are given below.

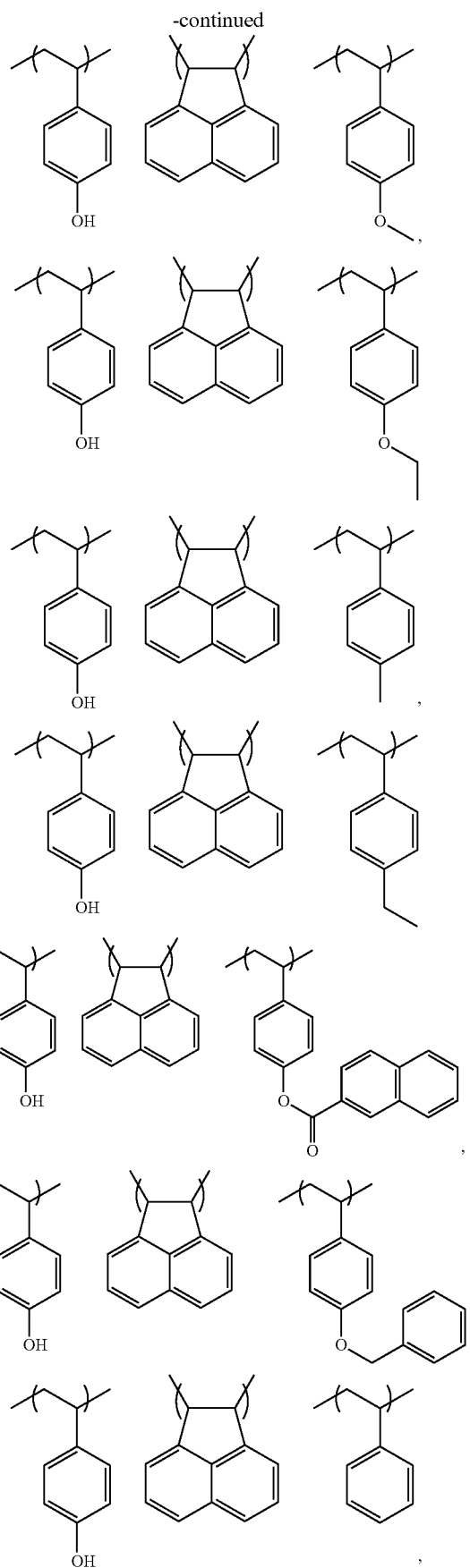

-continued

-continued

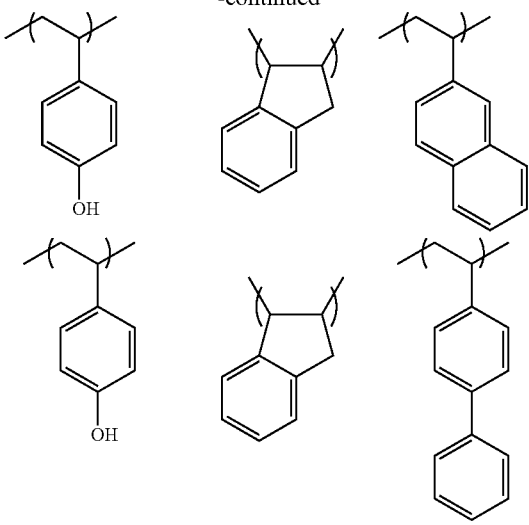

With respect to the contents of recurring units in the other polymer free of recurring units having formulae (1) and (2), an optimum combination of contents may be found in the ranges defined for the contents of recurring units other than formulae (1) and (2) in the polymer comprising recurring units having formula (1) and/or (2).

Also, when a blend of a polymer comprising recurring units having formula (1) and/or (2) and another polymer free of such units is used as the base polymer, the polymer comprising recurring units having formula (1) and/or (2) is preferably present in a content of at least 1%, more preferably at least 5% by weight based on the entire base polymer. If this content is less than 1 wt %, crosslinking reaction may not take place, or effects of reducing undercut and edge roughness may not be available. Since the polymer comprising recurring units having formula (1) and/or (2) may be used alone as the base polymer as described above, apparently the upper limit of its content is 100%. When it is desired to achieve fine adjustment of a pattern profile by blending the other polymer free of recurring units having formulae (1) and (2), the polymer comprising recurring units having formula (1) and/or (2) should preferably be present in a content of up to 99.5%, more preferably up to 98% by weight based on the entire base polymer. If this content is more than 99.5 wt %, no significant effects may be exerted by the addition of the other polymer free of recurring units having formulae (1) and (2).

The polymer for use in the chemically amplified negative resist composition of the invention may be prepared by effecting copolymerization of monomers by any well-known techniques with an optional combination of protection and deprotection reactions. The copolymerization reaction is preferably radical polymerization, but not limited thereto. With respect to the polymerization reaction, reference should be made to Patent Documents 1 to 5.

The polymer used as the base polymer in the chemically amplified negative resist composition generally has a weight average molecular weight (Mw) of 1,000 to 50,000, and preferably 1,000 to 20,000, as measured by gel permeation chromatography (GPC) using polystyrene standards. A polymer with a Mw of less than 1,000 may lead to a pattern having a rounded top, reduced resolution, and degraded LER as is well known in the art. If Mw is higher than 50,000, the pattern tends to have increased LER, depending on the pattern size to be resolved. The Mw is preferably controlled to 50,000 or less, more preferably 20,000 or less particularly when a pattern having a line width of up to 100 nm is formed.

The polymer used herein preferably has a narrow dispersity as demonstrated by a molecular weight distribution Mw/Mn in the range of 1.0 to 3.0, more preferably 1.0 to 2.5. A broader dispersity may cause drawbacks to the pattern such as foreign matter after development and degraded profile.

In the embodiment wherein a blend of a polymer comprising recurring units having formula (1) and/or (2) and another polymer free of such units is used as the base polymer, if the polymer comprising recurring units having formula (1) and/or (2) is present in a content of up to 20%, more specifically up to 10% by weight based on the entire base polymer, then the polymer comprising recurring units having formula (1) and/or (2) may be regarded as a crosslinker as used in conventional chemically amplified negative resist compositions. In this case, the polymer comprising recurring units having formula (1) and/or (2) may be either a polymer consisting of recurring units having formula (1) and/or (2) or a polymer comprising recurring units having formula (1) and/or (2) and recurring units selected from formulae (3) to (6). In the latter polymer comprising recurring units having formula (1) and/or (2) and recurring units selected from formulae (3) to (6), the content of recurring units having formula (1) and/or (2) is preferably 2 to 98 mol %, more preferably 5 to 95 mol %. With respect to the contents of recurring units having formulae (3) to (6), preferably the content of formula (3) is 2 to 98 mol %, and the sum of the contents of formulae (4), (5) and (6) is in a range of 0 to 40 mol %, and more preferably the content of formula (3) is 5 to 95 mol %, and the sum of the contents of formulae (4), (5) and (6) is in a range of 0 to 35 mol %. It is noted that as to the recurring units having formula (4) or (5) wherein the substituent group on aromatic ring is hydroxyl, the content of these recurring units should be merged into the content of recurring units having formula (3). The above definition that the content of formula (4) or (5) is preferably in a range of 0 to 40 mol %, more preferably 0 to 35 mol % is true only when the substituent group is not hydroxyl.

When the polymer is used in the range within which it may be regarded as a crosslinker, the polymer should preferably have a weight average molecular weight (Mw) of 500 to 50,000, and preferably 1,000 to 20,000, as measured by GPC using polystyrene standards. A polymer with Mw of less than 500 may not be significantly different from other crosslinkers. With Mw in excess of 50,000, the pattern tends to have increased LER.

When the polymer is used in the range within which it may be regarded as a crosslinker, a polymer serving as the base polymer (i.e., other than the polymer serving as crosslinker) may be a blend of a polymer comprising recurring units having formula (1) and/or (2) and a polymer free of recurring units having formula (1) and/or (2), or a polymer comprising recurring units having formula (1) and/or (2) or a blend thereof, or a polymer free of recurring units having formula (1) and/or (2) or a blend thereof.

Resist Composition

The chemically amplified negative resist composition of the invention is defined as comprising the inventive polymer as a base polymer in one embodiment, or as a crosslinker in another embodiment.

A low molecular weight crosslinker may be added to the chemically amplified negative resist composition. The low molecular weight crosslinker has two or more functional groups capable of electrophilic reaction with the polymer. While an acid which is generated by a PAG (to be described later) acts as a catalyst, the crosslinker at two or more sites reacts with the polymer to form crosslinks within the polymer and between polymer molecules for thereby rendering the polymer alkali insoluble. Typically reactive sites on the polymer subject to electrophilic reaction are aromatic rings or hydroxyl groups in constituent units of the polymer. A number of compounds are well known as the crosslinker (see Patent Documents 1 to 3).

As the crosslinker used herein, any well-known crosslinkers may be applicable. Suitable crosslinkers include alkoxymethylglycolurils and alkoxymethylmelamines. Exemplary of the alkoxymethylglycolurils are tetramethoxymethylglycoluril, 1,3-bismethoxymethyl-4,5-bismethoxyethyleneurea, and bismethoxymethylurea. Exemplary of the alkoxymethylmelamines are hexamethoxymethylmelamine and hexaethoxymethylmelamine.

The amount of the crosslinker added to the chemically amplified negative resist composition may be smaller since the polymer having a crosslink ability is already present therein. The crosslinker is preferably added in an amount of 0.1 to 6 parts, more preferably 0.5 to 3 parts by weight per 100 parts by weight of the base polymer. The addition of the crosslinker in this range helps increase the crosslinking efficiency of the polymer. If the amount of crosslinker is more than 6 parts by weight, the effect of LER being improved by incorporating recurring units having formula (1) and/or (2) into the polymer may be aggravated. The crosslinker may be used alone or in admixture of two or more.

Further an acid generator may be added to the chemically amplified negative resist composition. It is a compound which is decomposed to generate an acid upon exposure to high-energy radiation. A number of acid generators are known for use in chemically amplified resist compositions, as described in Patent Documents 1 to 6, for example. Generally any of these acid generators may be used. For use in the EB and EUV lithography, sulfonium base acid generators are useful, and a number of suitable compounds are also known. Further, the sulfonium base acid generator may take the form of a polymer having the acid generator incorporated in a side chain from its recurring unit as described in Patent Document 6.

Preferred examples of the acid generator which is not incorporated in a polymer are shown below, but not limited thereto.

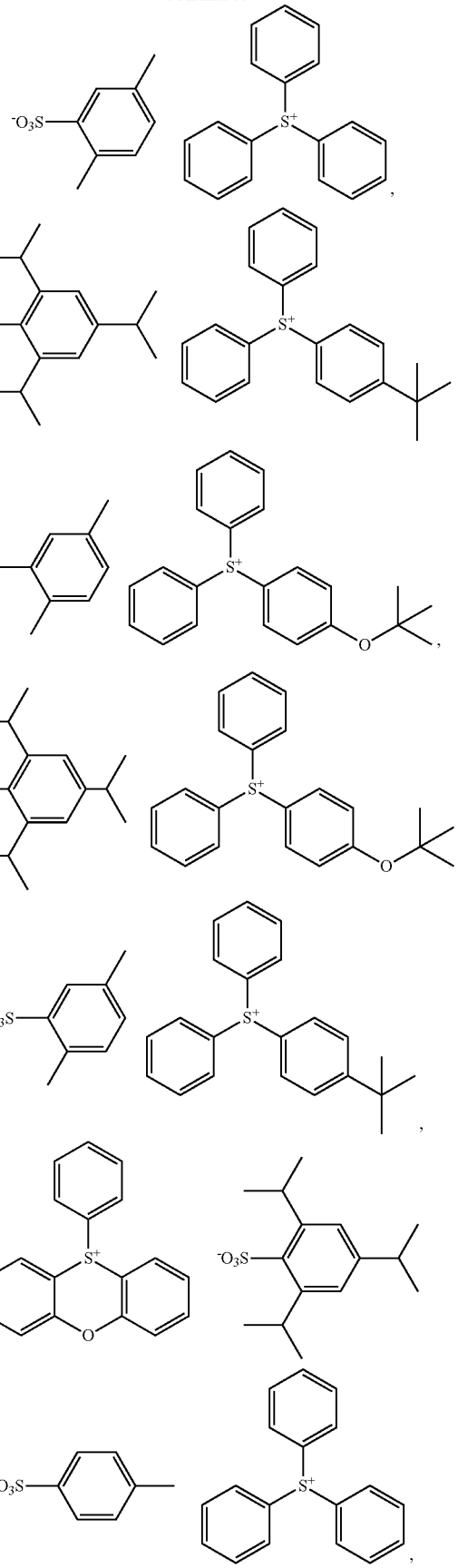

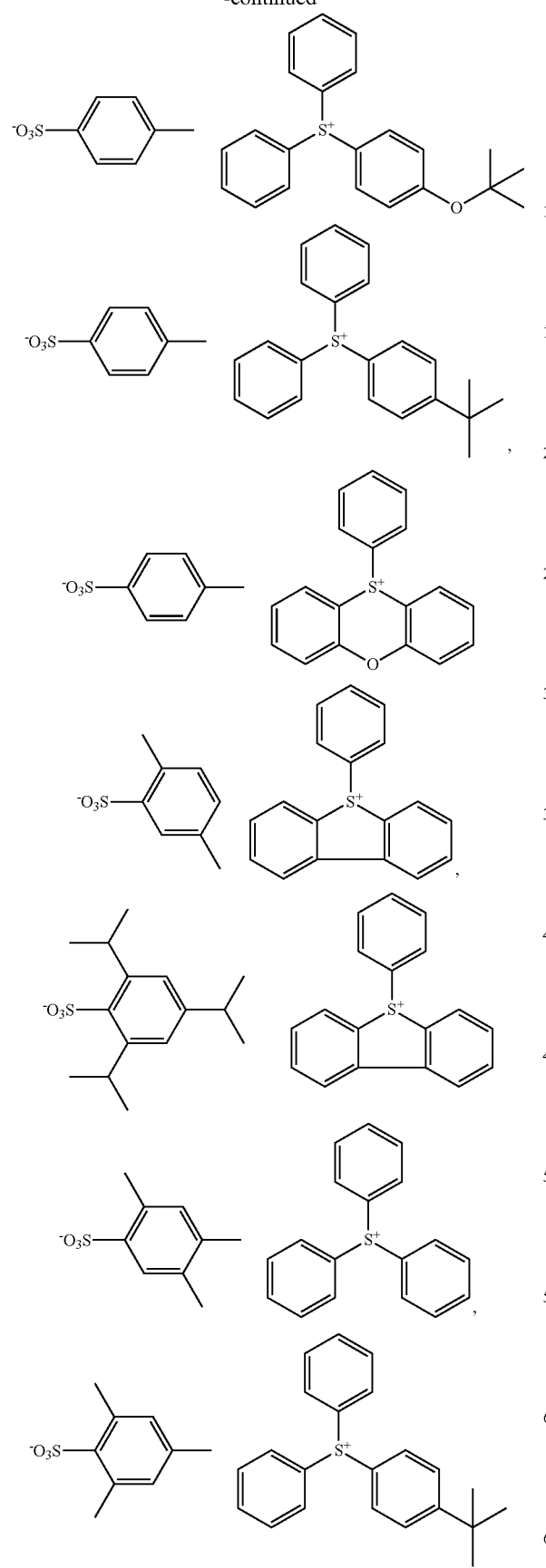
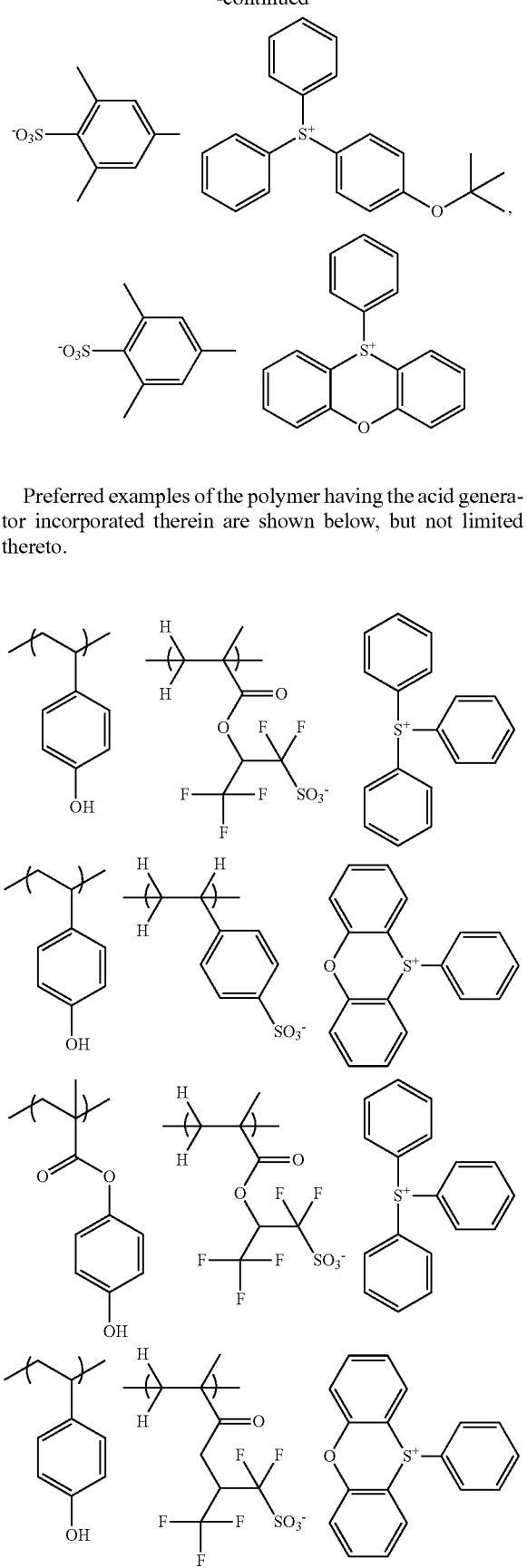
Preferred examples of the polymer having the acid generator incorporated therein are shown below, but not limited thereto.

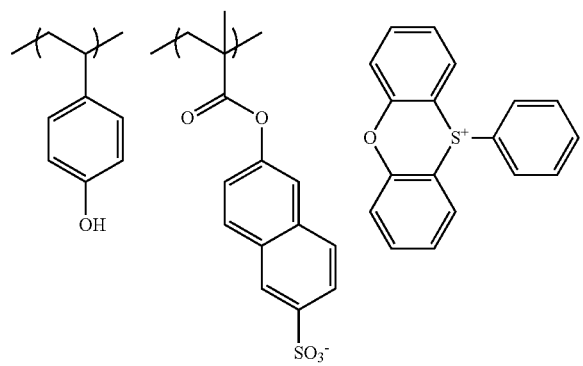
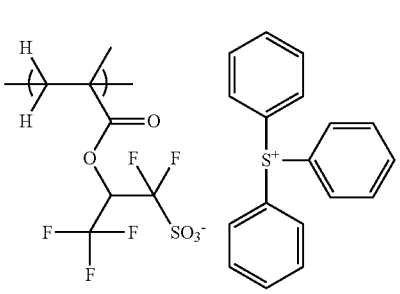
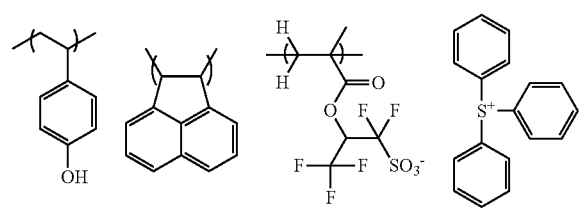
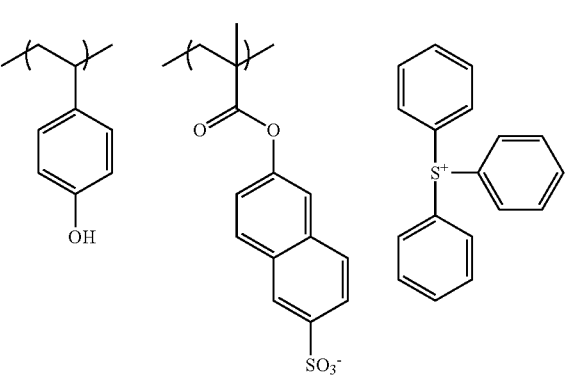
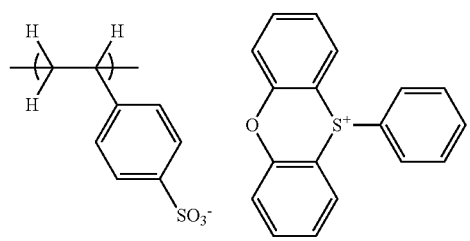
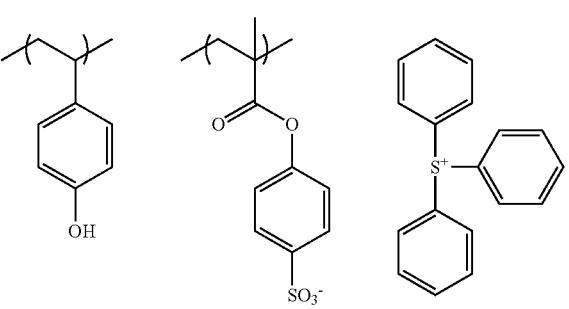
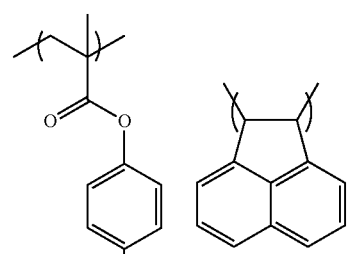
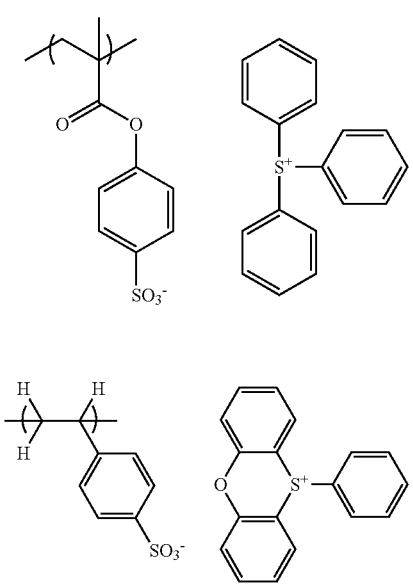
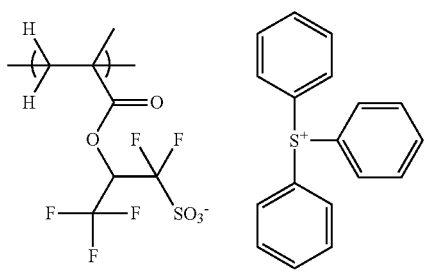
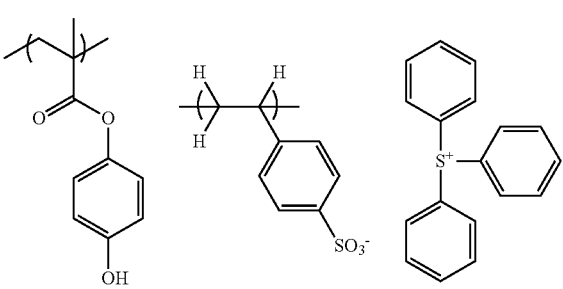

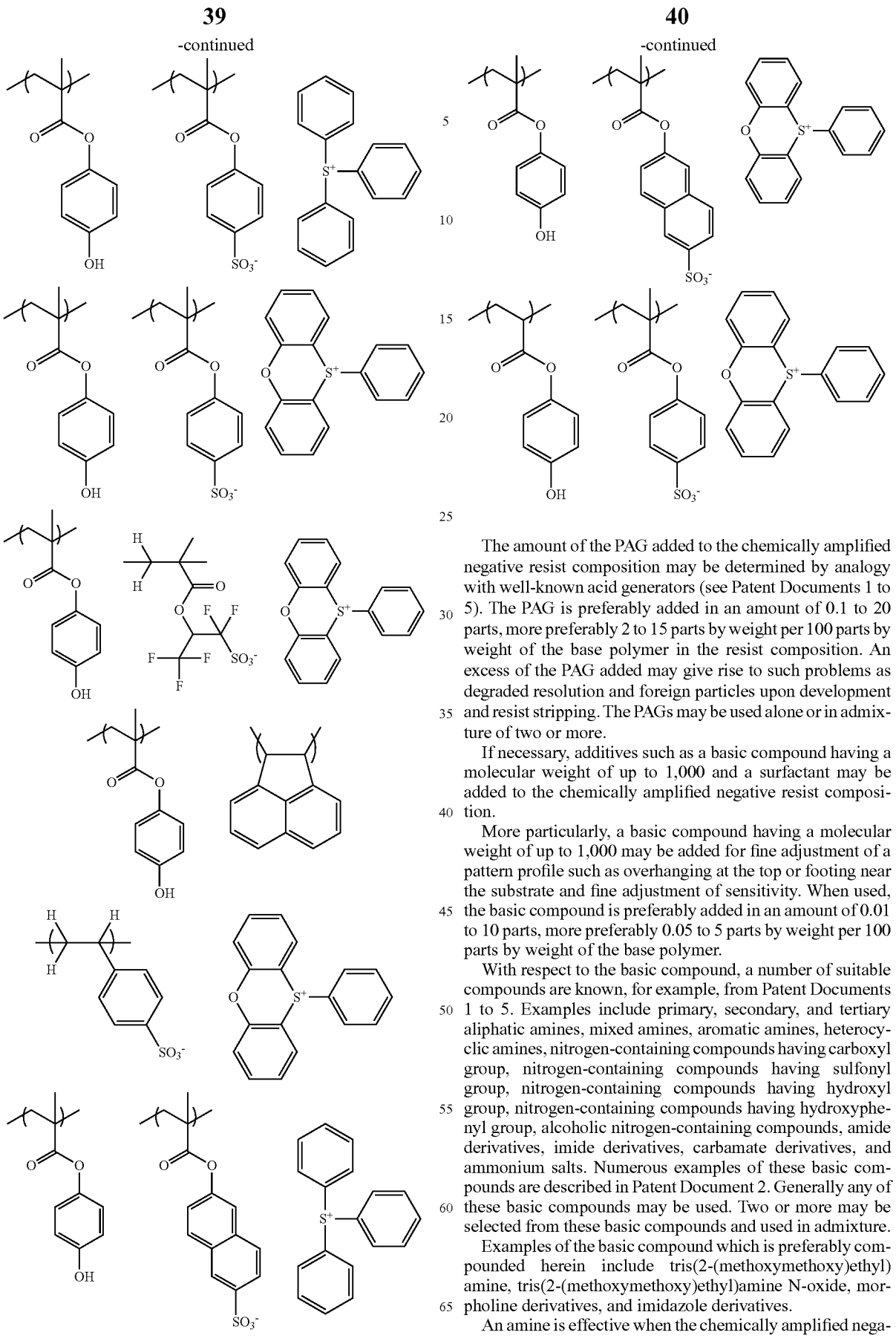

The amount of the PAG added to the chemically amplified negative resist composition may be determined by analogy with well-known acid generators (see Patent Documents 1 to 5). The PAG is preferably added in an amount of 0.1 to 20 parts, more preferably 2 to 15 parts by weight per 100 parts by weight of the base polymer in the resist composition. An excess of the PAG added may give rise to such problems as degraded resolution and foreign particles upon development and resist stripping. The PAGs may be used alone or in admixture of two or more.

If necessary, additives such as a basic compound having a molecular weight of up to 1,000 and a surfactant may be added to the chemically amplified negative resist composition.

More particularly, a basic compound having a molecular weight of up to 1,000 may be added for fine adjustment of a pattern profile such as overhanging at the top or footing near the substrate and fine adjustment of sensitivity. When used, the basic compound is preferably added in an amount of 0.01 to 10 parts, more preferably 0.05 to 5 parts by weight per 100 parts by weight of the base polymer.

With respect to the basic compound, a number of suitable compounds are known, for example, from Patent Documents 1 to 5. Examples include primary, secondary, and tertiary aliphatic amines, mixed amines, aromatic amines, heterocyclic amines, nitrogen-containing compounds having carboxyl group, nitrogen-containing compounds having sulfonyl group, nitrogen-containing compounds having hydroxyl group, nitrogen-containing compounds having hydroxyphenyl group, alcoholic nitrogen-containing compounds, amide derivatives, imide derivatives, carbamate derivatives, and ammonium salts. Numerous examples of these basic compounds are described in Patent Document 2. Generally any of these basic compounds may be used. Two or more may be selected from these basic compounds and used in admixture.

Examples of the basic compound which is preferably compounded herein include tris(2-(methoxymethoxy)ethyl)amine, tris(2-(methoxymethoxy)ethyl)amine N-oxide, morpholine derivatives, and imidazole derivatives.

An amine is effective when the chemically amplified negative resist composition is applied to a substrate, typically a substrate having a surface layer of chromium compound, which is susceptible to a phenomenon that the resist pattern is cut inward at the substrate interface during pattern formation, known as an undercut phenomenon. Although the chemically amplified negative resist composition of the invention itself has a potential to mitigate the phenomenon, an amine compound or amine oxide compound having a carboxyl group, but free of hydrogen in covalent bond with nitrogen serving as basic center (exclusive of those amine and amine oxide compounds whose nitrogen atom is contained in the cyclic structure of aromatic ring) is effectively used for improving the pattern profile.

Preferred examples of the amine or amine oxide compound having a carboxyl group, but free of hydrogen in covalent bond with nitrogen serving as basic center include compounds of the general formulae (7) to (9), but are not limited thereto.

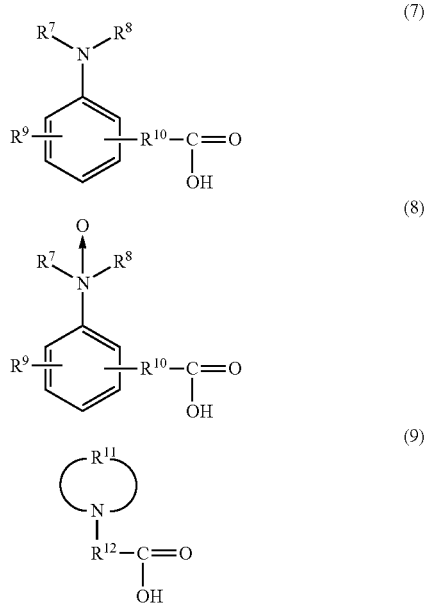

Herein $R^7$ and $R^8$ are each independently a straight, branched or cyclic $C_1$-$C_{20}$ alkyl group, $C_6$-$C_{20}$ aryl group, $C_7$-$C_{20}$ aralkyl group, $C_2$-$C_{10}$ hydroxyalkyl group, $C_2$-$C_{10}$ alkoxyalkyl group, $C_2$-$C_{10}$ acyloxyalkyl group, or $C_1$-$C_{10}$ alkylthioalkyl group. $R^7$ and $R^8$ may bond together to form a ring with the nitrogen atom to which they are attached, the ring being a 5 to 7-membered ring which may be substituted with alkyl or aryl. $R^9$ is hydrogen, a straight, branched or cyclic $C_1$-$C_{20}$ alkyl group, $C_6$-$C_{20}$ aryl group, $C_7$-$C_{20}$ aralkyl group, $C_1$-$C_{10}$ hydroxyalkyl group, $C_2$-$C_{10}$ alkoxyalkyl group, $C_2$-$C_{10}$ acyloxyalkyl group, $C_2$-$C_{10}$ alkylthioalkyl group, or halogen. $R^{10}$ is a single bond, a straight, branched or cyclic $C_1$-$C_{20}$ alkylene group, or $C_6$-$C_{20}$ arylene group. $R^{11}$ is an optionally substituted, straight or branched $C_2$-$C_{20}$ alkylene group whose carbon-carbon linkage may be separated by at least one carbonyl (—CO—), ether (—O—), ester (—COO—) or sulfide (—S—) group. $R^{12}$ is a straight, branched or cyclic $C_1$-$C_{20}$ alkylene group or $C_6$-$C_{20}$ arylene group.

Exemplary groups in these structural formulae are given below, but not limited thereto. Suitable straight, branched or cyclic $C_1$-$C_{20}$ alkyl groups include methyl, ethyl, propyl, isopropyl, butyl, isobutyl, t-butyl, pentyl, hexyl, decyl, cyclopentyl, cyclohexyl, and decahydronaphthalenyl. Suitable $C_6$-$C_{20}$ aryl groups include phenyl, naphthyl, anthryl, phenanthryl, pyrenyl, naphthacenyl, and fluorenyl. Suitable $C_7$-$C_{20}$ aralkyl groups include benzyl, phenethyl, phenylpropyl, naphthylmethyl, naphthylethyl, and anthracenylmethyl. Suitable $C_1$-$C_{10}$ hydroxyalkyl groups include hydroxymethyl, hydroxyethyl, and hydroxypropyl. Suitable $C_2$-$C_{10}$ alkoxyalkyl groups include methoxymethyl, 2-methoxyethyl, ethoxymethyl, 2-ethoxyethyl, propoxymethyl, 2-propoxyethyl, butoxymethyl, 2-butoxyethyl, amyloxymethyl, 2-amyloxyethyl, cyclohexyloxymethyl, 2-cyclohexyloxyethyl, cyclopentyloxymethyl, 2-cyclopentyloxyethyl, and isomers of their alkyl moiety. Suitable $C_2$-$C_{10}$ acyloxyalkyl groups include formyloxymethyl, acetoxymethyl, propionyloxymethyl, butyryloxymethyl, pivaloyloxymethyl, cyclohexanecarbonyloxymethyl, and decanoyloxymethyl. Suitable $C_2$-$C_{10}$ alkylthioalkyl groups include methylthiomethyl, ethylthiomethyl, propylthiomethyl, isopropylthiomethyl, butylthiomethyl, isobutylthiomethyl, t-butylthiomethyl, t-amylthiomethyl, decylthiomethyl, and cyclohexylthiomethyl. When $R^7$ and $R^8$ bond together to form a ring with the nitrogen atom to which they are attached, examples of the 5 to 7-membered ring include pyrrolidine, piperidine, imidazolidine, piperazine, morpholine, quinuclidine, indoline, isoindoline, carbazole, perimidine, phenoxazine, β-carboline, pyrrole, imidazole, indole, indazole, isoindole, and purine rings.

Preferred examples of the amine compound of formula (7) include, but are not limited thereto, o-dimethylaminobenzoic acid, p-dimethylaminobenzoic acid, m-dimethylaminobenzoic acid, p-diethylaminobenzoic acid, p-dipropylaminobenzoic acid, p-dibutylaminobenzoic acid, p-dipentylaminobenzoic acid, p-dihexylaminobenzoic acid, p-diethanolaminobenzoic acid, p-diisopropanolaminobenzoic acid, p-dimethanolaminobenzoic acid, 2-methyl-4-diethylaminobenzoic acid, 2-methoxy-4-diethylaminobenzoic acid, 3-dimethylamino-2-naphthalenic acid, 3-diethylamino-2-naphthalenic acid, 2-dimethylamino-5-bromobenzoic acid, 2-dimethylamino-5-chlorobenzoic acid, 2-dimethylamino-5-iodobenzoic acid, 2-dimethylamino-5-hydroxybenzoic acid, 4-dimethylaminophenylacetic acid, 4-dimethylaminophenylpropionic acid, 4-dimethylaminophenylbutyric acid, 4-dimethylaminophenylmalic acid, 4-dimethylaminophenylpyruvic acid, 4-dimethylaminophenyllacetic acid, 2-(4-dimethylaminophenyl)benzoic acid, and 2-(4-(dibutylamino)-2-hydroxybenzoyl)benzoic acid.

The amine oxide compound of formula (8) corresponds to the oxidized form of the amine compound of formula (7). Preferred examples of the amine oxide compound of formula (8) include oxidized forms of exemplary amine compounds of formula (7), but are not limited thereto.

Preferred examples of the amine compound of formula (9) include, but are not limited thereto, 1-piperidinepropionic acid, 1-piperidinebutyric acid, 1-piperidinemalic acid, 1-piperidinepyruvic acid, and 1-piperidinelactic acid.

Some of the compounds having an amine oxide structure represented by formula (8) are existing and some are novel compounds. They may be prepared by selecting an optimum method in accordance with a particular structure. Exemplary non-limiting methods include oxidizing reaction of a nitrogen-containing compound using an oxidizing agent and oxidizing reaction of a nitrogen-containing compound in a hydrogen peroxide water diluted solution. These methods are described below in detail.

One exemplary method for preparing a nitrogen-containing alcohol compound is shown below. This method is applicable to the synthesis of a compound of formula (9).

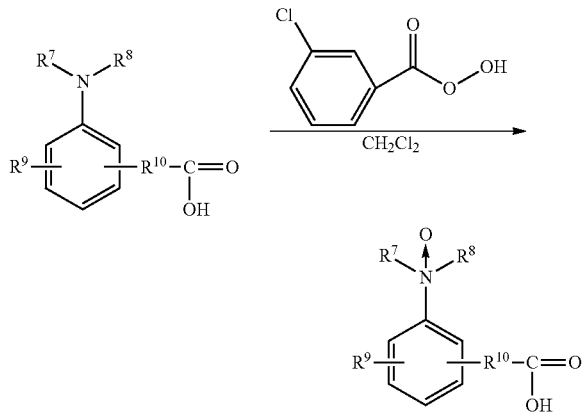

Herein R$^7$ to R$^{10}$ are as defined above.

This reaction is an oxidizing reaction of an amine using an oxidizing agent, m-chloroperbenzoic acid. The reaction may be performed using other oxidizing agents commonly employed in standard oxidizing reaction. Following the reaction, the reaction mixture may be purified by standard techniques such as distillation, chromatography and recrystallization. Reference is made to Patent Document 7.

To the resist composition, any of surfactants commonly used for improving coating characteristics may be added. A number of surfactants are well known and described in Patent Documents 1 to 6 and any suitable one may be selected therefrom.

In the resist composition, the surfactant is preferably formulated in an amount of up to 3 parts, and more preferably up to 1 part by weight, per 100 parts by weight of the base polymer. When used, the surfactant is preferably added in an amount of at least 0.01 part by weight.

An organic solvent may be used in the preparation of the resist composition. It may be any of organic solvents in which the polymer, acid generator and other additives are dissolvable. Suitable organic solvents include, but are not limited to, ketones such as cyclohexanone and methyl n-amyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; and lactones such as γ-butyrolactone. These solvents may be used alone or in admixture. Of these solvents, ethyl lactate, propylene glycol monomethyl ether, PGMEA, and mixtures thereof are preferred because the acid generator is most soluble therein.

In the negative resist composition, the organic solvent is preferably used in an amount of 500 to 10,000 parts by weight, more preferably 1,000 to 9,700 parts by weight per 100 parts by weight of the base polymer. When adjusted to such a concentration, the resist composition is applicable by a spin coating technique to form a resist film having a thickness of 10 to 300 nm and an improved flatness in a consistent manner.

Process

Pattern formation using the chemically amplified negative resist composition of the invention may be performed by well-known lithography processes. The process generally involves coating, prebaking, exposure to high-energy radiation, PEB, and development with alkaline developer. The resist composition is first applied onto a substrate for IC fabrication (e.g., Si, SiO$_2$, SiN, SiON, TiN, WSi, BPSG, SOG, organic antireflective coating or the like) or a substrate for mask circuit fabrication (e.g., Cr, CrO, CrON, MoSi or the like) by a suitable coating technique such as spin coating. The coating is prebaked on a hot plate at a temperature of 60 to 150° C. for 1 to 10 minutes, preferably 80 to 140° C. for 1 to 5 minutes to form a resist film of 0.05 to 2.0 μm thick.

Then the resist film is exposed to high-energy radiation, typically deep UV, excimer laser, x-ray or EUV through a mask having a desired pattern. Alternatively, a pattern is written on the resist film directly with EB. The exposure dose is preferably 1 to 200 mJ/cm$^2$, more preferably 10 to 100 mJ/cm$^2$. The exposure may be performed by conventional lithography whereas the immersion lithography of holding a liquid between the mask and the resist film may be employed if desired. In this case, a protective film which is insoluble in water may be applied on the resist film. The resist film is then baked (PEB) on a hot plate at 60 to 150° C. for 1 to 10 minutes, preferably 80 to 140° C. for 1 to 5 minutes. Thereafter the resist film is developed with a developer in the form of an aqueous base solution, for example, 0.1 to 5 wt %, preferably 1.5 to 3 wt % aqueous solution of tetramethylammonium hydroxide (TMAH) for 0.1 to 3 minutes, preferably 0.5 to 2 minutes by conventional techniques such as dip, puddle and spray techniques. In this way, a desired resist pattern is formed on the substrate.

It is known that when the substrate has on its surface a film of a nitrogen-containing material such as SiN, SiON, MoSiN, MoSiON or TiN, an attempt to apply a chemically amplified negative resist composition on the substrate and process the film to form a pattern often encounters an undercut phenomenon. When the substrate has on its surface a film of a chromium base material such as Cr, CrO or CrON (optionally containing carbon), a serious undercut phenomenon occurs. Quite unexpectedly, the undercut phenomenon can be substantially controlled when a resist film of the chemically amplified negative resist composition of the invention is processed to form a pattern.

The chemically amplified negative resist composition comprising a base polymer comprising recurring units selected from formulae (1) to (6) has many advantages. The resist film resulting therefrom has high etch resistance. Also the resist composition is effective when it is required that the pattern experience a minimal change of line width even when the duration between exposure and PEB is prolonged. The resist composition is effectively applicable to a processable substrate, specifically a substrate having a surface layer of material to which a resist film is less adherent and which is likely to invite pattern stripping or pattern collapse, and particularly a substrate having sputter deposited thereon a surface layer material susceptible to pattern collapse, typically metallic chromium or a chromium compound containing at least one light element selected from oxygen, nitrogen and carbon. For this reason, the resist composition is effective in processing photomask blanks by EB lithography.

EXAMPLE

Synthesis Examples, Examples, and Comparative Examples are given below by way of illustration and not by way of limitation. The average molecular weights including weight average molecular weight (Mw) and number average molecular weight (Mn) are determined by gel permeation chromatography (GPC) versus polystyrene standards, from which a dispersity (Mw/Mn) is computed. Me stands for methyl. The compositional ratio of a copolymer is on a molar basis.

Monomer Synthesis Example 1

Synthesis of 1,3-bismethoxymethyl-2-oxohexahydropyrimidin-5-yl methacrylate (Z-1)

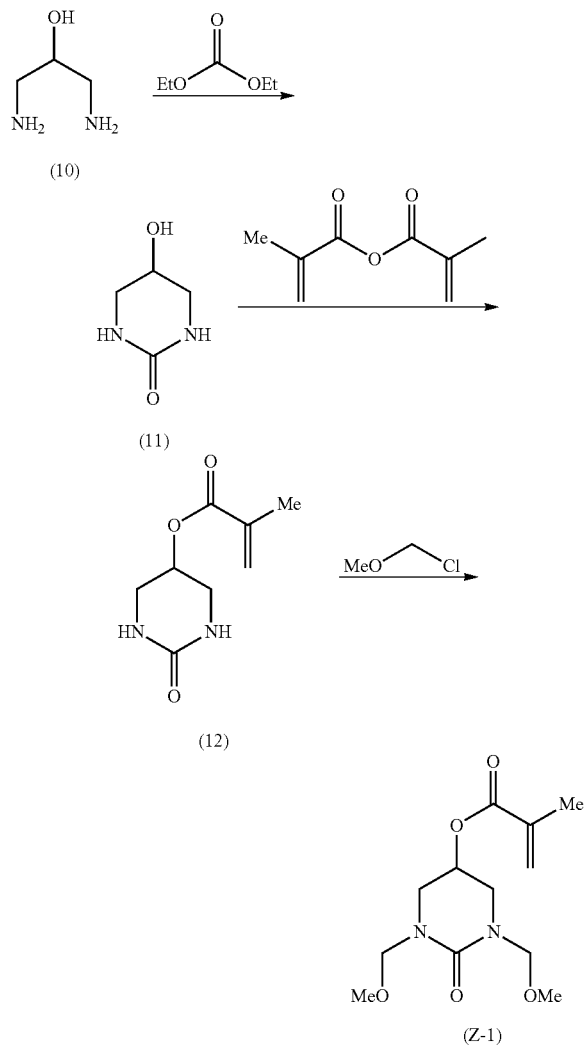

Monomer Synthesis Example 1-1

Synthesis of 5-hydroxytetrahydropyrimidin-2-one (11)

A mixture of 49.1 g of 1,3-diamino-2-propanol (10), 64.4 g of diethyl carbonate, and 3.79 g of 1,5,7-triazabicyclo[4.4.0]dec-5-ene was stirred and heated under reflux for 6 hours. Stirring was continued for a further 10 hours while gradually removing ethanol formed during reaction. Thereafter, the solvent and diethyl carbonate were distilled off in vacuum, obtaining 64.4 g of the end compound, 5-hydroxytetrahydropyrimidin-2-one (11). Yield 100%. The end compound was used in the subsequent step without further purification.

$^1$H-NMR (600 MHz in CDCl$_3$): δ=2.91 (2H, dd), 3.13 (2H, dd), 3.81 (1H, tt), 5.96 (2H, s) ppm Monomer Synthesis Example 1-2

Synthesis of 2-oxohexahydropyrimidin-5-yl methacrylate (12)

In a solvent mixture of 45.0 g of tetrahydrofuran (THF) and 36.0 g of H$_2$O was dissolved 9.0 g of 5-hydroxytetrahydropyrimidin-2-one (11) obtained in Monomer Synthesis Example 1-1. To the solution, 17.2 g of methacrylic anhydride and 17.8 g of 25 wt % NaOH aqueous solution were added dropwise below 30° C. Stirring was continued at the temperature for 3 hours, followed by ordinary aqueous work-up. The crude product thus obtained was dissolved in CH$_3$CN and added dropwise to diisopropyl ether, obtaining 8.3 g of the end compound, 2-oxohexahydropyrimidin-5-yl methacrylate (12). Yield 60%.

IR (thin film): ν=3246, 3102, 1682, 1540, 1438, 1299, 1183, 1176, 1146, 1082, 947 cm$^{-1}$ $^1$H-NMR (600 MHz in CDCl$_3$): δ=1.87 (3H, t), 3.18 (2H, dd), 3.37 (2H, dd), 5.00 (1H, t), 5.71 (1H, dq), 6.02 (1H, q), 6.15 (2H, d) ppm Monomer Synthesis Example 1-3

Synthesis of 1,3-bismethoxymethyl-2-oxohexahydropyrimidin-5-yl methacrylate (Z-1)

To 80 g of CH$_3$CN were added 5.3 g of diisopropylethylamine, 10.0 g of 2-oxohexahydropyrimidin-5-yl methacrylate (12) obtained in Monomer Synthesis Example 1-2, and 20.0 g of sodium iodide. To the mixture, 11.0 g of chloromethyl methyl ether was added dropwise below 10° C. After the dropwise addition, the reaction mixture was warmed to room temperature and stirred for 5 hours, followed by ordinary aqueous work-up. The product was purified by silica gel column chromatography, obtaining 7.5 g of the target compound, 1,3-bismethoxymethyl-2-oxohexahydropyrimidin-5-yl methacrylate (Z-1). Yield 51%.

IR (thin film): ν=2948, 1716, 1645, 1497, 1450, 1388, 1313, 1293, 1214, 1163, 1094, 1069, 1038, 905 cm$^{-1}$ $^1$H-NMR (600 MHz in CDCl$_3$): δ=1.87 (3H, t), 3.14 (3H, s), 3.42 (2H, dd), 3.65 (2H, dd), 4.60 (2H, d), 4.77 (2H, d), 5.20 (1H, dd), 5.71 (1H, q), 6.02 (1H, q) ppm Monomer Synthesis Example 2

Synthesis of 1,3-bismethoxymethyl-2-oxohexahydropyrimidin-5-yl 4-vinylbenzoate (Z-2)

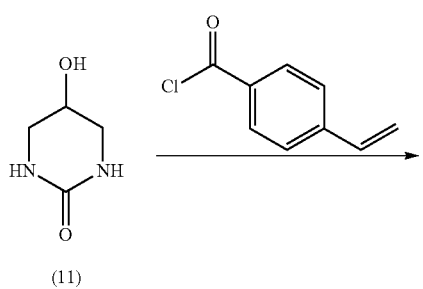

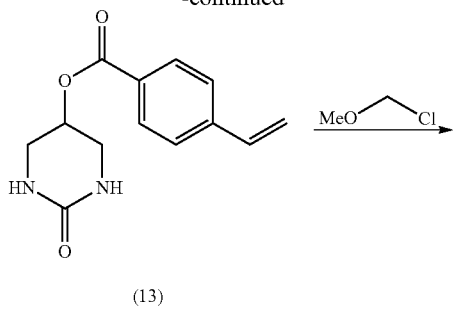

(13)

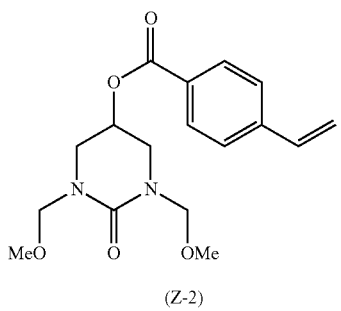

(Z-2)

Monomer Synthesis Example 2-1

Synthesis of 2-oxohexahydropyrimidin-5-yl 4-vinylbenzoate (13)

In a solvent mixture of 50.0 g of tetrahydrofuran (THF) and 40.0 g of $H_2O$ was dissolved 10.0 g of 5-hydroxytetrahydropyrimidin-2-one (11) obtained in Monomer Synthesis Example 1-1. To the solution, 21.5 g of 4-vinylbenzoic acid chloride and 20.7 g of 25 wt % NaOH aqueous solution were added dropwise below 30° C. Stirring was continued at the temperature for 3 hours, followed by ordinary aqueous work-up. The crude product thus obtained was dissolved in $CH_3CN$ and added dropwise to diisopropyl ether, obtaining 13.8 g of the end compound, 2-oxohexahydropyrimidin-5-yl 4-vinylbenzoate (13). Yield 65%.

Monomer Synthesis Example 2-2

Synthesis of 1,3-bismethoxymethyl-2-oxohexahydropyrimidin-5-yl 4-vinylbenzoate (Z-2)

To 84.0 g of $CH_3CN$ were added 36.2 g of diisopropylethylamine, 13.8 g of 2-oxohexahydropyrimidin-5-yl 4-vinylbenzoate (13) obtained in Monomer Synthesis Example 2-1, and 20.9 g of sodium iodide. To the mixture, 11.3 g of chloromethyl methyl ether was added dropwise below 30° C. Stirring was continued at the temperature for 5 hours, followed by ordinary aqueous work-up. The product was purified by silica gel column chromatography, obtaining 10.3 g of the target compound, 1,3-bismethoxymethyl-2-oxohexahydropyrimidin-5-yl 4-vinylbenzoate (Z-2). Yield 55%.

Monomer Synthesis Example 3

Synthesis of 1,3-bismethoxymethyl-2-oxohexahydropyrimidin-5-yl 6-vinyl-2-naphthalenecarboxylate (Z-3)

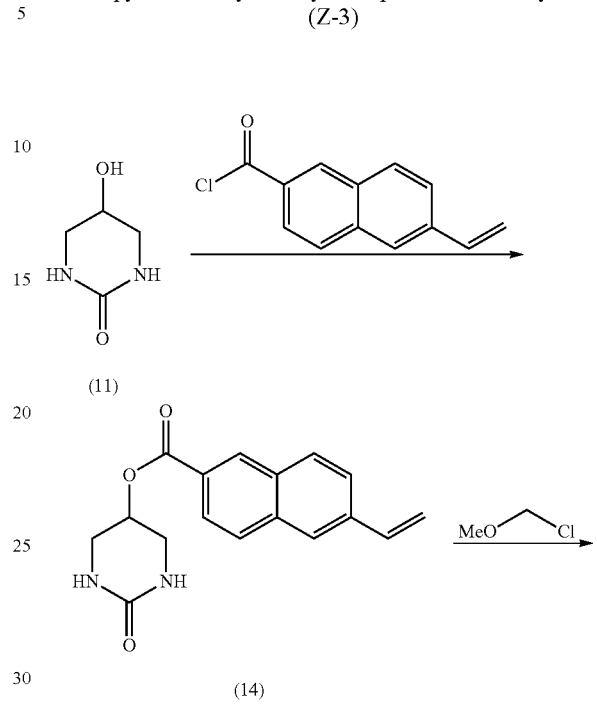

(Z-3)

The target compound, 1,3-bismethoxymethyl-2-oxohexahydropyrimidin-5-yl 6-vinyl-2-naphthalenecarboxylate (Z-3) was synthesized by the same procedure as in Monomer Synthesis Example 2 except that 6-vinyl-2-naphthalenecarboxylic acid chloride was used instead of 4-vinylbenzoic acid chloride.

Polymer Synthesis Example 1

In a 250-mL dropping funnel under nitrogen blanket, a solution was prepared by adding 48.2 g of 4-acetoxystyrene, 6.0 g of 4-methylstyrene, 6.5 g of acenaphthylene, 9.3 g of the polymerizable crosslinker Z-1, and 7.8 g of dimethyl 2,2'-azobis(2-methylpropionate) (V601, Wako Pure Chemical Industries, Ltd.) to 82.0 g of toluene as solvent. Under nitrogen blanket, a 1-L polymerization flask was charged with 82.0 g of toluene and heated at 80° C., to which the solution was added dropwise over 4 hours. After the completion of dropwise addition, the reaction solution was stirred for 18 hours for polymerization while maintaining the temperature of 80° C., and then cooled to room temperature. The polymerization solution was added dropwise to 1,000 g of hexane whereupon a copolymer precipitate was collected by filtration. The copolymer thus separated was washed twice with 200 g of a hexane/toluene (10/1) mixture. In a 1-L flask under nitrogen blanket, the copolymer was dissolved in a solvent mixture of 126 g of tetrahydrofuran and 42 g of methanol. 18.1 g of ethanolamine was added to the solution, which was stirred at 60° C. for 5 hours. The reaction solution was concentrated in vacuum and dissolved in a mixture of 300 g of ethyl acetate and 80 g of water. The resulting solution was transferred to a separatory funnel along with 9.1 g of acetic acid, followed by separatory operation. With the lower layer discarded, the organic layer was combined with 80 g of water and 12.1 g of pyridine and subjected to separatory operation. With the lower layer discarded, the organic layer was subjected to water washing/separation using 80 g of water. The water washing/separation was repeated 5 times in total. More definite phase separation was achieved by adding 20 g of acetone and stirring for some time during the standing period on every separatory operation.

The organic layer resulting from the separatory operation was concentrated and dissolved in 140 g of acetone. The acetone solution was passed through a nylon filter having a pore size of 0.02 μm, and added dropwise to 2,800 g of water for precipitation. The crystalline precipitate was filtered, washed with water, and suction filtered for 2 hours. The resulting mass was again dissolved in 150 g of acetone. The acetone solution was passed through a nylon filter having a pore size of 0.02 μm, and added dropwise to 2,800 g of water for precipitation. The crystalline precipitate was filtered, washed with water, and dried, obtaining 42.0 g of a white polymer. The polymer was analyzed by $^{13}$C-NMR, $^1$H-NMR and GPC, with the analytical data shown below.

copolymer composition

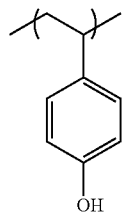

70

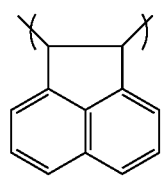

12

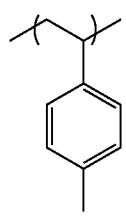

60

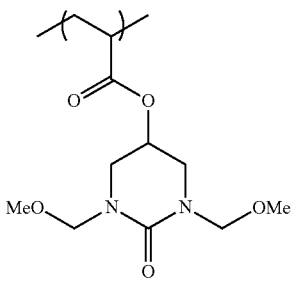

8

Copolymer composition (molar ratio)

4-hydroxystyrene:acenaphthylene:4-methylstyrene:Z-1=70:10:12:8

Mw=4,500

Mw/Mn=1.82

This is designated Polymer #1.

Polymer Synthesis Example 2

In a 2000-mL dropping funnel under nitrogen blanket, a solution was prepared by adding 187 g of 4-hydroquinone monomethacrylate, 27 g of acenaphthylene, 46 g of 4-methylstyrene, 38 g of the polymerizable crosslinker Z-1, and 33 g of dimethyl 2,2'-azobis(2-methylpropionate) (V601, Wako Pure Chemical Industries, Ltd.) to 400 g of methyl ethyl ketone as solvent. Under nitrogen blanket, a 2000-mL polymerization flask was charged with 300 g of methyl ethyl ketone and heated at 80° C., to which the solution was added dropwise over 4 hours. After the completion of dropwise addition, the reaction solution was stirred for 16 hours for polymerization while maintaining the temperature of 80° C., and then cooled to room temperature. The polymerization solution was added dropwise to 7,000 g of hexane whereupon a copolymer precipitate was collected by filtration. The copolymer thus separated was washed twice with 1,500 g of hexane. The resulting mass was again dissolved in 700 g of methyl ethyl ketone. The MEK solution was passed through a nylon filter having a pore size of 0.02 μm, and added dropwise to 7,000 g of hexane for precipitation. The copolymer precipitate was filtered, washed twice with 1,500 g of hexane, and dried, obtaining 260 g of a white polymer. The polymer was analyzed by $^{13}$C-NMR, $^1$H-NMR and GPC, with the analytical data shown below.

copolymer composition

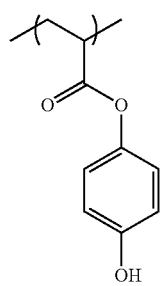

60

-continued

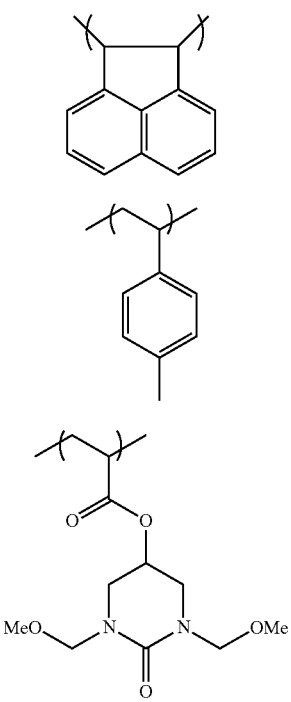

Copolymer composition (molar ratio)
4-hydroquinone mono-methacrylate:acenaphthylene:4-methylstyrene: Z-1=60:10:22:8
Mw=4,300
Mw/Mn=1.75
This is designated Polymer #8.

Polymer Synthesis Examples 3 to 19

Polymers #2 to #7, #9 to #19 were prepared by the same procedure as in Polymer Synthesis Examples 1 and 2 except that the type and amount of monomers were changed. In Table 1, the ratio is a molar ratio of each unit incorporated in a polymer.

TABLE 1

| Resin | Unit 1 | ratio | Unit 2 | ratio | Unit 3 | ratio | Unit 4 | ratio |
|---|---|---|---|---|---|---|---|---|
| Polymer 1 | A-1 | 0.70 | B-3 | 0.12 | C-2 | 0.10 | Z-1 | 0.08 |
| Polymer 2 | A-1 | 0.65 | B-3 | 0.12 | C-2 | 0.15 | Z-1 | 0.08 |
| Polymer 3 | A-1 | 0.65 | B-3 | 0.12 | C-2 | 0.11 | Z-1 | 0.12 |
| Polymer 4 | A-1 | 0.66 | B-3 | 0.12 | C-1 | 0.14 | Z-1 | 0.08 |
| Polymer 5 | A-1 | 0.66 | B-1 | 0.12 | C-2 | 0.14 | Z-1 | 0.08 |
| Polymer 6 | A-1 | 0.66 | B-2 | 0.12 | C-2 | 0.14 | Z-1 | 0.08 |
| Polymer 7 | A-1 | 0.66 | B-4 | 0.12 | C-2 | 0.14 | Z-1 | 0.08 |
| Polymer 8 | A-2 | 0.60 | B-3 | 0.22 | C-2 | 0.10 | Z-1 | 0.08 |
| Polymer 9 | A-2 | 0.60 | B-1 | 0.22 | C-2 | 0.10 | Z-1 | 0.08 |
| Polymer 10 | A-2 | 0.60 | B-2 | 0.22 | C-2 | 0.10 | Z-1 | 0.08 |
| Polymer 11 | A-2 | 0.60 | B-4 | 0.22 | C-2 | 0.10 | Z-1 | 0.08 |
| Polymer 12 | A-3 | 0.77 | B-3 | 0.07 | C-2 | 0.08 | Z-1 | 0.08 |
| Polymer 13 | A-1 | 0.66 | B-3 | 0.12 | C-2 | 0.14 | Z-2 | 0.08 |
| Polymer 14 | A-1 | 0.66 | B-3 | 0.12 | C-2 | 0.14 | Z-3 | 0.08 |
| Polymer 15 | A-1 | 0.70 | Z-1 | 0.30 | | | | |
| Polymer 16 | A-2 | 0.70 | Z-1 | 0.30 | | | | |
| Polymer 17 | A-1 | 0.50 | Z-1 | 0.50 | | | | |
| Polymer 18 | A-2 | 0.50 | Z-1 | 0.50 | | | | |
| Polymer 19 | Z-1 | 1.00 | | | | | | |

Units 1 to 4 in Table 1 have the structure shown below.

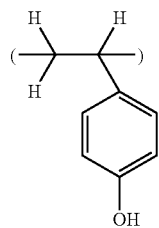
A-1

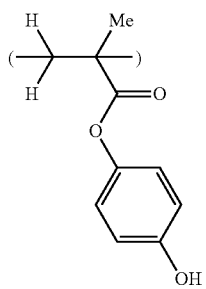
A-2

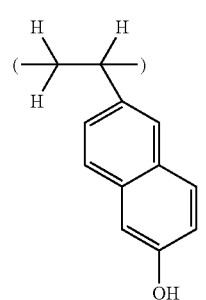
A-3

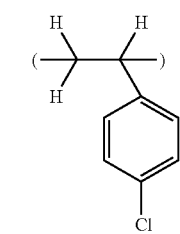
B-1

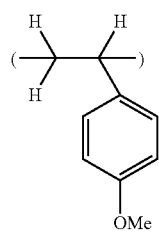
B-2

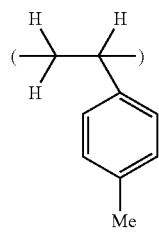
B-3

B-4

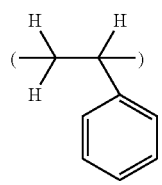

C-1

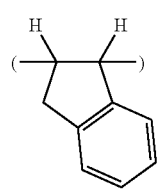

C-2

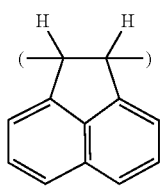

Z-1

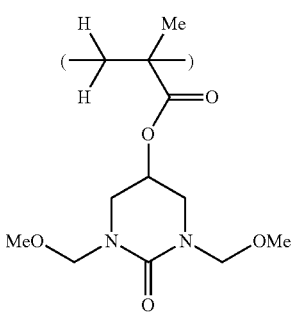

Z-2

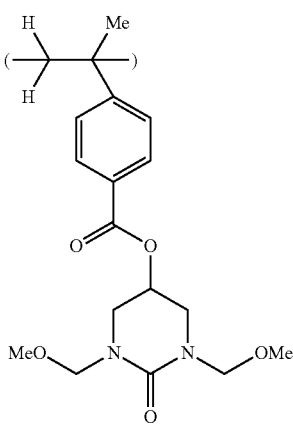

Z-3

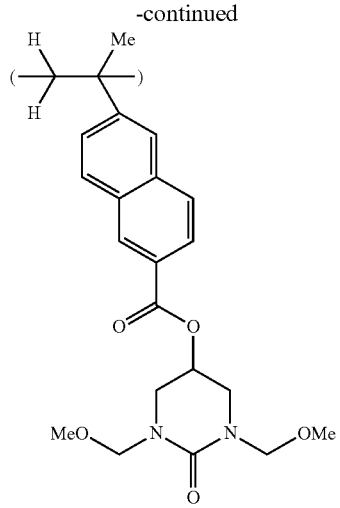

Examples and Comparative Examples

Preparation of Negative Resist Compositions

Chemically amplified negative resist compositions were prepared by using inventive polymers (Polymers #1 to #19) or other polymers (Polymers K and M), and dissolving the polymer, an acid generator (PAG-A or PAG-B), a basic compound (Base-1 or Base-2), and optionally tetramethoxymethylglycoluril (TMGU) as crosslinker in an organic solvent mixture in accordance with the recipe shown in Tables 2 and 3. These compositions were each filtered through a nylon or UPE filter having a pore size of 0.02 μm, thereby giving negative resist composition solutions.

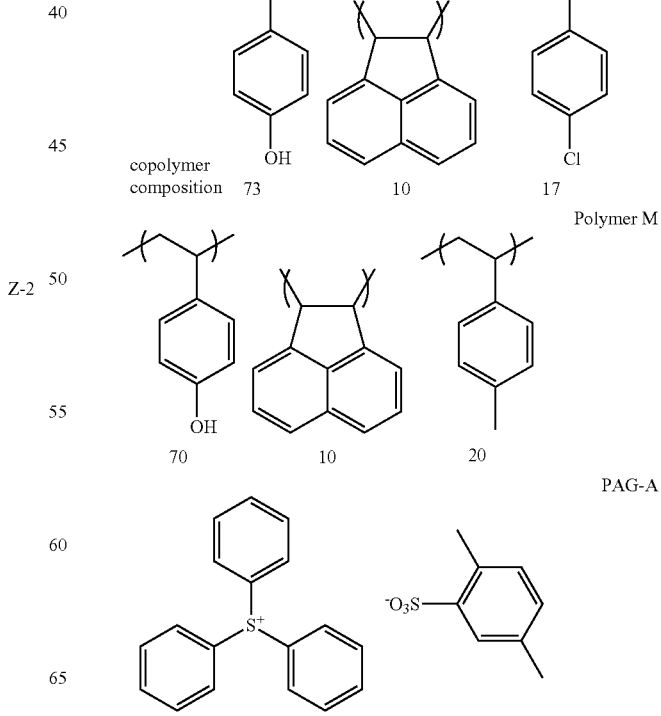

-continued

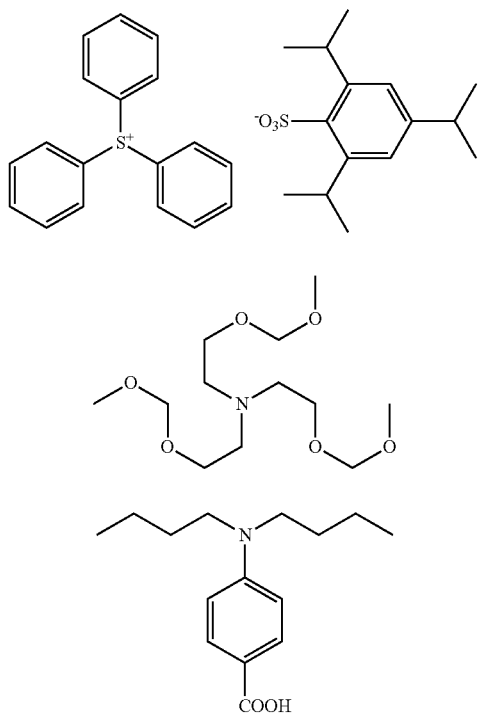

PAG-B

Base-1

Base-2

The organic solvents 1 and 2 used were propylene glycol monomethyl ether acetate (PGMEA) and ethyl lactate (EL). Each solution further contained 0.075 pbw of 3-methyl-3-(2,2,2-trifluoroethoxymethyl)oxetane/tetrahydrofuran/2,2-dimethyl-1,3-propanediol copolymer (structural formula shown below, available from Omnova Solutions, Inc.) as surfactant relative to 80 pbw of the polymer.

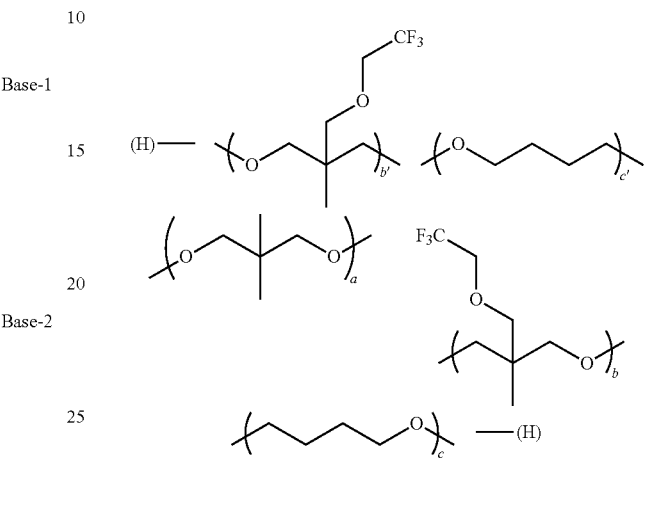

$a:(b+b'):(c+c')=1:4$ to $7:0.01$ to $1$ (molar ratio) Mw=1,500

TABLE 2

| | Resin (pbw) | Acid generator (pbw) | Basic compound (pbw) | Crosslinker (pbw) | Solvent 1 (pbw) | Solvent 2 (pbw) |
|---|---|---|---|---|---|---|
| Example 1 | Polymer 1 (80) | PAG-A (8) PAG-B (2) | Base-1 (1.1) | — | PGMEA (1,109) | EL (2,587) |
| Example 2 | Polymer 2 (80) | PAG-A (8) PAG-B (2) | Base-1 (1.5) | — | PGMEA (1,109) | EL (2,587) |
| Example 3 | Polymer 2 (80) | PAG-A (8) PAG-B (2) | Base-1 (1.5) | TMGU (2.0) | PGMEA (1,109) | EL (2,587) |
| Example 4 | Polymer 2 (80) | PAG-B (10) | Base-1 (1.5) | — | PGMEA (1,109) | EL (2,587) |
| Example 5 | Polymer 2 (80) | PAG-A (8) PAG-B (2) | Base-1 (1.2) Base-2 (0.3) | — | PGMEA (1,109) | EL (2,587) |
| Example 6 | Polymer 2 (80) | PAG-B (10) | Base-1 (1.2) Base-2 (0.3) | — | PGMEA (1,109) | EL (2,587) |
| Example 7 | Polymer 3 (80) | PAG-A (8) PAG-B (2) | Base-1 (1.5) | — | PGMEA (1,109) | EL (2,587) |
| Example 8 | Polymer 4 (80) | PAG-A (8) PAG-B (2) | Base-1 (1.5) | — | PGMEA (1,109)) | EL (2,587) |
| Example 9 | Polymer 5 (80) | PAG-A (8) PAG-B (2) | Base-1 (1.5) | — | PGMEA (1,109) | EL (2,587) |
| Example 10 | Polymer 6 (80) | PAG-A (8) PAG-B (2) | Base-1 (1.5) | — | PGMEA (1,109) | EL (2,587) |
| Example 11 | Polymer 7 (80) | PAG-A (8) PAG-B (2) | Base-1 (1.5) | — | PGMEA (1,109) | EL (2,587) |
| Example 12 | Polymer 8 (80) | PAG-A (8) PAG-B (2) | Base-1 (1.5) | — | PGMEA (1,109) | EL (2,587) |
| Example 13 | Polymer 9 (80) | PAG-A (8) PAG-B (2) | Base-1 (1.5) | — | PGMEA (1,109) | EL (2,587) |
| Example 14 | Polymer 10 (80) | PAG-A (8) PAG-B (2) | Base-1 (1.5) | — | PGMEA (1,109) | EL (2,587) |
| Example 15 | Polymer 11 (80) | PAG-A (8) PAG-B (2) | Base-1 (1.5) | — | PGMEA (1,109) | EL (2,587) |
| Example 16 | Polymer 12 (80) | PAG-A (8) PAG-B (2) | Base-1 (1.5) | — | PGMEA (1,109) | EL (2,587) |

TABLE 2-continued

|  | Resin (pbw) | Acid generator (pbw) | Basic compound (pbw) | Crosslinker (pbw) | Solvent 1 (pbw) | Solvent 2 (pbw) |
|---|---|---|---|---|---|---|
| Example 17 | Polymer 13 (80) | PAG-A (8) PAG-B (2) | Base-1 (1.5) | — | PGMEA (1,109) | EL (2,587) |
| Example 18 | Polymer 14 (80) | PAG-A (8) PAG-B (2) | Base-1 (1.5) | — | PGMEA (1,109) | EL (2,587) |

*pbw: parts by weight

TABLE 3

|  | Resin (pbw) | Acid generator (pbw) | Basic compound (pbw) | Crosslinker (pbw) | Solvent 1 (pbw) | Solvent 2 (pbw) |
|---|---|---|---|---|---|---|
| Example 19 | Polymer K (80) | PAG-A (8) PAG-B (2) | Base-1 (1.5) | Polymer 15 (25) | PGMEA (1,109) | EL (2,587) |
| Example 20 | Polymer M (80) | PAG-A (8) PAG-B (2) | Base-1 (1.5) | Polymer 15 (25) | PGMEA (1,109) | EL (2,587) |
| Example 21 | Polymer K (80) | PAG-A (8) PAG-B (2) | Base-1 (1.5) | Polymer 16 (25) | PGMEA (1,109) | EL (2,587) |
| Example 22 | Polymer M (80) | PAG-A (8) PAG-B (2) | Base-1 (1.5) | Polymer 16 (25) | PGMEA (1,109) | EL (2,587) |
| Example 23 | Polymer K (80) | PAG-A (8) PAG-B (2) | Base-1 (1.5) | Polymer 17 (15) | PGMEA (1,109) | EL (2,587) |
| Example 24 | Polymer M (80) | PAG-A (8) PAG-B (2) | Base-1 (1.5) | Polymer 17 (15) | PGMEA (1,109) | EL (2,587) |
| Example 25 | Polymer K (80) | PAG-A (8) PAG-B (2) | Base-1 (1.5) | Polymer 18 (15) | PGMEA (1,109) | EL (2,587) |
| Example 26 | Polymer M (80) | PAG-A (8) PAG-B (2) | Base-1 (1.5) | Polymer 18 (15) | PGMEA (1,109) | EL (2,587) |
| Example 27 | Polymer M (80) | PAG-A (8) PAG-B (2) | Base-1 (1.5) | Polymer 19 (8) | PGMEA (1,109) | EL (2,587) |
| Comparative Example 1 | Polymer K (80) | PAG-A (8) PAG-B (2) | Base-1 (1.5) | TMGU (8.154) | PGMEA (1,109) | EL (2,587) |
| Comparative Example 2 | Polymer M (80) | PAG-A (8) PAG-B (2) | Base-1 (1.5) | TMGU (8.154) | PGMEA (1,109) | EL (2,587) |

*pbw: parts by weight

Evaluation of EB Image Writing

Using a coater/developer system Clean Track ACT-M (Tokyo Electron Ltd.), each of the negative resist compositions was spin-coated onto a 152-mm square mask blank having a chromium oxynitride film at the outermost surface and prebaked on a hot plate at 110° C. for 600 seconds to form a resist film of 80 nm thick. The thickness of the resist film was measured by an optical film thickness measurement system Nanospec (Nanometrics Inc.). Measurement was made at 81 points in the plane of the blank substrate excluding a peripheral band extending 10 mm inward from the blank periphery, and an average film thickness and a film thickness range were computed therefrom.

The coated mask blanks were exposed to electron beam using an EB writer system EBM-5000Plus (NuFlare Technology Inc., accelerating voltage 50 keV), then baked (PEB) at 120° C. for 600 seconds, and developed with a 2.38 wt % tetramethylammonium hydroxide aqueous solution, thereby yielding negative patterns.

The patterned wafer was observed under a top-down scanning electron microscope (TDSEM). The optimum exposure (Eop) was defined as the exposure dose (μC/cm$^2$) which provided a 1:1 resolution at the top and bottom of a 200-nm 1:1 line-and-space pattern. The maximum resolution of the resist was defined as the minimum line width of a line-and-space pattern that could be resolved and separated at the optimum exposure. The LER of a 100-nm line-and-space pattern was measured under SEM. On observation in cross section of the resist pattern under SEM, it was visually judged whether or not the pattern profile was rectangular. Table 4 tabulates the test results of the inventive and comparative resist compositions on EB image writing.

TABLE 4

|  | Eop (μC/cm$^2$) | Maximum resolution (nm) | LER (nm) | Pattern profile |
|---|---|---|---|---|
| Example 1 | 25 | 45 | 4.7 | rectangular |
| Example 2 | 25 | 40 | 4.4 | rectangular |
| Example 3 | 22 | 40 | 4.6 | rectangular |
| Example 4 | 30 | 40 | 4.5 | rectangular |
| Example 5 | 26 | 40 | 4.4 | rectangular |
| Example 6 | 30 | 40 | 4.5 | rectangular |
| Example 7 | 22 | 45 | 4.5 | rectangular |
| Example 8 | 25 | 45 | 4.7 | rectangular |
| Example 9 | 32 | 45 | 4.8 | rectangular |
| Example 10 | 24 | 40 | 4.5 | rectangular |
| Example 11 | 27 | 40 | 4.5 | rectangular |
| Example 12 | 26 | 45 | 4.6 | rectangular |
| Example 13 | 32 | 45 | 4.8 | rectangular |
| Example 14 | 25 | 45 | 4.6 | rectangular |
| Example 15 | 28 | 45 | 4.7 | rectangular |
| Example 16 | 26 | 45 | 4.6 | rectangular |
| Example 17 | 25 | 40 | 4.5 | rectangular |
| Example 18 | 25 | 40 | 4.5 | rectangular |
| Example 19 | 31 | 45 | 4.6 | rectangular |
| Example 20 | 25 | 40 | 4.5 | rectangular |
| Example 21 | 31 | 45 | 4.7 | rectangular |

TABLE 4-continued

|  | Eop ($\mu C/cm^2$) | Maximum resolution (nm) | LER (nm) | Pattern profile |
|---|---|---|---|---|
| Example 22 | 25 | 40 | 4.6 | rectangular |
| Example 23 | 31 | 45 | 4.7 | rectangular |
| Example 24 | 25 | 40 | 4.6 | rectangular |
| Example 25 | 31 | 45 | 4.8 | rectangular |
| Example 26 | 25 | 40 | 4.6 | rectangular |
| Example 27 | 25 | 40 | 4.5 | rectangular |
| Comparative Example 1 | 35 | 60 | 5.9 | undercut |
| Comparative Example 2 | 28 | 55 | 5.5 | rectangular |

It is evident from Table 4 that the chemically amplified negative resist composition of the invention tends to exhibit a higher sensitivity than the resist composition having an ordinary crosslinker (TMGU) added thereto, provided that the base polymers in these resist compositions are of the same construction except the presence or absence of recurring units derived from a polymerizable crosslinker (e.g., compare Example 2 with Comparative Example 2, or Example 9 with Comparative Example 1). This indicates that the crosslinker-incorporated polymer is increased in crosslinking efficiency. Since crosslinking groups are uniformly distributed throughout the resist film, the chemically amplified negative resist composition comprising the crosslinker-incorporated polymer as a base polymer is improved in resolution and LER. Where the inventive polymer is used as an additive or crosslinker (Examples 19 to 27), similarly improved performance is demonstrated. Therefore, the chemically amplified negative resist composition of the invention is suited as ultrafine pattern-forming material for VLSI fabrication and mask pattern-forming material by EB lithography.

Japanese Patent Application No. 2010-169482 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A polymer comprising recurring units of at least one selected from recurring units having a N,N'-bis(alkoxymethyl)tetrahydropyrimidinone or N,N'-bis(hydroxymethyl)tetrahydropyrimidinone structure on a side chain, represented by the general formulae (1) and (2):

$$(1)$$

$$(2)$$

wherein A is hydrogen, fluorine, methyl or trifluoromethyl, $R^1$ is hydrogen or a monovalent, straight, branched or cyclic $C_1$-$C_6$ alkyl group, $R^2$ is each independently a monovalent, straight, branched or cyclic $C_1$-$C_6$ alkyl group which may contain oxygen, or halogen, a is an integer of 0 to 4, and p is an integer of 0 to 2.

2. The polymer of claim 1, further comprising recurring units having the general formula (3):

$$(3)$$

wherein A is as defined for formulae (1) and (2), Q is a single bond, methylene group, or $C_2$-$C_{10}$ alkylene group which may contain an ether bond at an intermediate of the chain, $R^3$ is each independently a straight, branched or cyclic $C_1$-$C_6$ alkyl group, b is an integer of 0 to 4, c is an integer of 1 to 5, r is 0 or 1, and q is an integer of 0 to 2.

3. The polymer of claim 1, further comprising recurring units of at least one selected from recurring units represented by the general formulae (4) and (5):

$$(4)$$

$$(5)$$

wherein $R^4$ is each independently hydroxyl, halogen, an optionally halo-substituted, straight, branched or cyclic $C_2$-$C_8$ acyloxy group, an optionally halo-substituted, straight, branched or cyclic $C_1$-$C_6$ alkyl group, or an optionally halo-substituted, straight, branched or cyclic $C_1$-$C_6$ alkoxy group, and d is an integer of 0 to 4.

4. The polymer of claim 1, further comprising recurring units having the general formula (6):

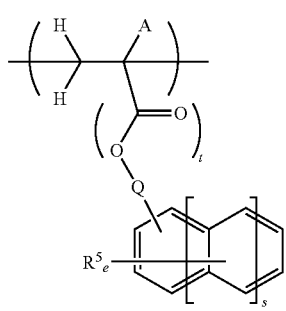
(6)

wherein A is as defined for formulae (1) and (2) and Q is a single bond, methylene group, or $C_2$-$C_{10}$ alkylene group which may contain an ether bond at an intermediate of the chain, $R^5$ is halogen, an optionally halo-substituted monovalent $C_1$-$C_{20}$ hydrocarbon or hydrocarbonoxy group, or a monovalent $C_2$-$C_{15}$ hydrocarbon-carbonyloxy group, t is 0 or 1, s is an integer of 0 to 2, and e is an integer of 0 to 5.

5. A chemically amplified negative resist composition comprising the polymer of claim 1 as a base polymer.

6. The resist composition of claim 5, further comprising a polymer free of recurring units represented by formulae (1) and (2) as a second base polymer.

7. The resist composition of claim 6 wherein the polymer free of recurring units represented by formulae (1) and (2) is a polymer comprising recurring units of at least one selected from recurring units represented by formulae (3) to (6):

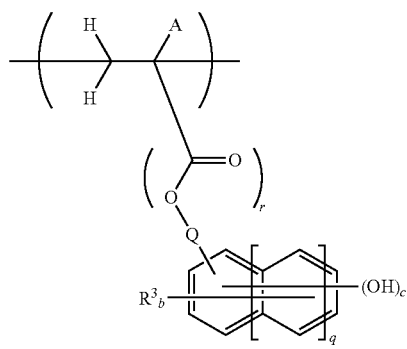
(3)

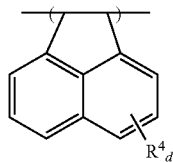
(4)

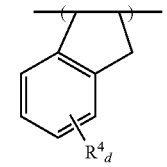
(5)

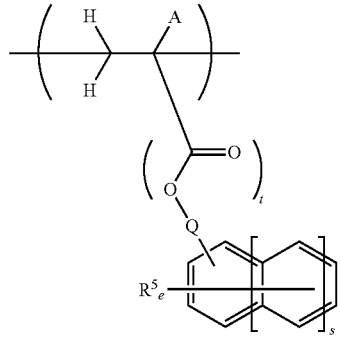
(6)

wherein Q is a single bond, methylene group, or $C_2$-$C_{10}$ alkylene group which may contain an ether bond at an intermediate of the chain, $R^3$ is each independently a straight, branched or cyclic $C_1$-$C_6$ alkyl group, b is an integer of 0 to 4, c is an integer of 1 to 5, r is 0 or 1, and q is an integer of 0 to 2, wherein $R^4$ is each independently hydroxyl, halogen, an optionally halo-substituted, straight, branched or cyclic $C_2$-$C_8$ acyloxy group, an optionally halo-substituted, straight, branched or cyclic $C_1$-$C_6$ alkyl group or an optionally halo-substituted, straight, branched or cyclic $C_1$-$C_6$ alkoxy group, and d is an integer of 0 to 4, and wherein $R^5$ is halogen, an optionally halo-substituted monovalent $C_1$-$C_{20}$ hydrocarbon or hydrocarbonoxy group, or a monovalent $C_2$-$C_{15}$ hydrocarbon-carbonyloxy group, t is 0 or 1, s is an integer of 1 to 2 and e is an integer of 0 to 5.

8. A chemically amplified negative resist composition comprising the polymer of claim 1 as a crosslinker.

9. A process for forming a pattern, comprising the steps of:
applying the chemically amplified negative resist composition of claim 5 onto a processable substrate to form a resist film,
exposing patternwise the resist film to high-energy radiation, and
developing the exposed resist film with an alkaline developer.

10. The process of claim 9 wherein the processable substrate is a photomask blank.

* * * * *